United States Patent
Oberg et al.

(10) Patent No.: US 12,214,159 B2
(45) Date of Patent: Feb. 4, 2025

(54) INSULIN INFUSION SET

(71) Applicant: Capillary Biomedical, Inc., Irvine, CA (US)

(72) Inventors: Keith A. Oberg, Newhall, CA (US);
Mark C. Estes, Malibu, CA (US);
Kenneth C. Hsu, Tustin, CA (US);
David S. Gillett, San Diego, CA (US)

(73) Assignee: Tandem Diabetes Care, Inc, San Diego, CA (US)

( * ) Notice: Subject to any disclaimer, the term of this patent is extended or adjusted under 35 U.S.C. 154(b) by 313 days.

(21) Appl. No.: 17/446,271

(22) Filed: Aug. 27, 2021

(65) Prior Publication Data
US 2022/0226568 A1    Jul. 21, 2022

Related U.S. Application Data

(60) Provisional application No. 63/071,994, filed on Aug. 28, 2020.

(51) Int. Cl.
*A61M 5/158* (2006.01)
*A61M 5/142* (2006.01)

(52) U.S. Cl.
CPC ........ *A61M 5/158* (2013.01); *A61M 5/14248* (2013.01); *A61M 2005/14252* (2013.01); *A61M 2005/1585* (2013.01); *A61M 2005/1587* (2013.01)

(58) Field of Classification Search
CPC .. A61M 2005/1587; A61M 2005/1585; A61M 2005/14252; A61M 5/14248; A61M 5/158
See application file for complete search history.

(56) References Cited

U.S. PATENT DOCUMENTS

| | | | |
|---|---|---|---|
| 4,498,843 A | 2/1985 | Schneider et al. |
| 4,703,756 A | 11/1987 | Gough et al. |
| 4,755,173 A | 7/1988 | Konopka et al. |
| 4,777,953 A | 10/1988 | Ash et al. |
| 4,952,207 A | 8/1990 | Lemieux |
| 5,002,054 A | 3/1991 | Ash et al. |

(Continued)

FOREIGN PATENT DOCUMENTS

| CA | 2659005 C | 4/2014 |
|---|---|---|
| CA | 2950966 C | 7/2019 |

(Continued)

OTHER PUBLICATIONS

Bryant, J., Fluid dynamics—Equation of continuity and Bernoulli's principle; retrieved from the internet at http://www.physics.usyd.edu.au/~jbryant/Fluids/Fluidslect4.pdf on Apr. 2, 2015; 37 pages.

(Continued)

*Primary Examiner* — Tiffany Legette

(57) ABSTRACT

Embodiments of devices and methods to maintain preservative concentration in a medication delivered using a medical device are provided. A barrier layer can be used to prevent migration of preservatives. A vent can be used to allow release of preservatives prior to delivery to the patient. An absorbent element can be used to maintain preservative concentration at a desired level. A filter can be used to capture particulates from the medication prior to delivery to a patient.

42 Claims, 14 Drawing Sheets

(56) References Cited

U.S. PATENT DOCUMENTS

| | | |
|---|---|---|
| 5,176,662 A | 1/1993 | Bartholomew et al. |
| 5,425,723 A | 6/1995 | Wang |
| 5,545,152 A | 8/1996 | Funderburk et al. |
| 5,584,831 A | 12/1996 | McKay |
| 5,704,926 A | 1/1998 | Sutton |
| 5,848,996 A | 12/1998 | Eldor |
| 5,869,774 A | 2/1999 | Backlund et al. |
| 5,879,367 A | 3/1999 | Latterell et al. |
| 5,899,891 A | 5/1999 | Racz |
| 5,919,369 A | 7/1999 | Ash |
| 5,925,018 A | 7/1999 | Ungerstedt |
| 5,947,953 A | 9/1999 | Ash et al. |
| 5,995,860 A | 11/1999 | Sun et al. |
| 6,017,361 A | 1/2000 | Mikus et al. |
| 6,030,358 A | 2/2000 | Odland |
| 6,042,561 A | 3/2000 | Ash et al. |
| 6,042,576 A | 3/2000 | De Vries |
| 6,049,727 A | 4/2000 | Crothall |
| 6,056,718 A | 5/2000 | Funderburk et al. |
| 6,122,536 A | 9/2000 | Sun et al. |
| 6,179,816 B1 | 1/2001 | Mattola et al. |
| 6,261,272 B1 | 7/2001 | Gross et al. |
| 6,302,866 B1 | 10/2001 | Marggi |
| 6,304,766 B1 | 10/2001 | Colvin, Jr. |
| 6,471,689 B1 | 10/2002 | Joseph et al. |
| 6,488,663 B1 | 12/2002 | Steg |
| 6,537,241 B1 | 3/2003 | Odland |
| 6,572,542 B1 | 6/2003 | Houben et al. |
| 6,572,586 B1 | 6/2003 | Wojcik |
| 6,585,695 B1 | 7/2003 | Adair et al. |
| 6,618,603 B2 | 9/2003 | Varalli et al. |
| 6,702,857 B2 | 3/2004 | Brauker et al. |
| 6,736,797 B1 | 5/2004 | Larsen et al. |
| 6,749,589 B1 | 6/2004 | Douglas et al. |
| 6,770,030 B1 | 8/2004 | Schaupp et al. |
| 6,800,451 B2 | 10/2004 | Daniloff et al. |
| 6,805,683 B1 | 10/2004 | Johansson |
| 6,830,562 B2 | 12/2004 | Mogensen |
| 6,855,136 B2 | 2/2005 | Dorros et al. |
| 6,862,534 B2 | 3/2005 | Sterling et al. |
| 6,929,618 B1 | 8/2005 | Johansson |
| 6,940,590 B2 | 9/2005 | Colvin, Jr. et al. |
| 6,989,891 B2 | 1/2006 | Braig et al. |
| 7,009,180 B2 | 3/2006 | Sterling et al. |
| 7,022,071 B2 | 4/2006 | Schaupp et al. |
| 7,052,483 B2 | 5/2006 | Wojcik |
| 7,070,580 B2 | 7/2006 | Nielsen |
| 7,128,727 B2 | 10/2006 | Flaherty et al. |
| 7,147,623 B2 | 12/2006 | Mathiasen |
| 7,157,723 B2 | 1/2007 | Colvin, Jr. et al. |
| 7,211,068 B2 | 5/2007 | Douglas |
| 7,235,350 B2 | 6/2007 | Schulman et al. |
| 7,248,912 B2 | 7/2007 | Gough et al. |
| 7,255,687 B2 | 8/2007 | Huang et al. |
| 7,309,325 B2 | 12/2007 | Mulier et al. |
| 7,336,984 B2 | 2/2008 | Gough et al. |
| 7,364,592 B2 | 4/2008 | Carr-Brendel et al. |
| 7,588,558 B2 | 9/2009 | Sage, Jr. et al. |
| 7,593,108 B2 | 9/2009 | Sterling et al. |
| 7,613,491 B2 | 11/2009 | Boock et al. |
| 7,621,395 B2 | 11/2009 | Mogensen et al. |
| 7,637,918 B2 | 12/2009 | Dant |
| 7,651,845 B2 | 1/2010 | Doyle et al. |
| 7,666,172 B2 | 2/2010 | Atil |
| 7,686,787 B2 | 3/2010 | Moberg et al. |
| 7,699,808 B2 | 4/2010 | Marrs et al. |
| 7,722,537 B2 | 5/2010 | Sterling et al. |
| 7,744,570 B2 | 6/2010 | Fangrow, Jr. |
| 7,800,078 B2 | 9/2010 | Colvin, Jr. et al. |
| 7,822,450 B2 | 10/2010 | Colvin, Jr. et al. |
| 7,867,199 B2 | 1/2011 | Mogensen et al. |
| 7,867,200 B2 | 1/2011 | Mogensen et al. |
| 7,871,456 B2 | 1/2011 | Gough et al. |
| 7,875,008 B2 | 1/2011 | Chong et al. |
| 7,894,870 B1 | 2/2011 | Lucisano et al. |
| 7,905,877 B1 | 3/2011 | Jimenez et al. |
| 7,931,621 B2 | 4/2011 | Cross et al. |
| 7,935,092 B1 | 5/2011 | Odland et al. |
| 7,939,332 B2 | 5/2011 | Colvin, Jr. |
| 7,951,357 B2 | 5/2011 | Gross et al. |
| 7,985,199 B2 | 7/2011 | Komerup et al. |
| 8,012,126 B2 | 9/2011 | Tipsmark et al. |
| 8,043,229 B2 | 10/2011 | Mulvihill et al. |
| 8,062,250 B2 | 11/2011 | Mogensen et al. |
| 8,073,548 B2 | 12/2011 | Colvin, Jr. et al. |
| 8,114,064 B2 | 2/2012 | Alferness et al. |
| 8,143,068 B2 | 3/2012 | Colvin, Jr. et al. |
| 8,157,773 B2 | 4/2012 | Tashjian |
| 8,172,805 B2 | 5/2012 | Mogensen et al. |
| 8,204,565 B2 | 6/2012 | Arnold et al. |
| 8,206,343 B2 | 6/2012 | Racz |
| 8,229,546 B2 | 7/2012 | Falkén et al. |
| 8,273,061 B2 | 9/2012 | McConnell et al. |
| 8,273,228 B2 | 9/2012 | Dall'Oglio et al. |
| 8,303,533 B2 | 11/2012 | Regittnig et al. |
| 8,318,193 B2 | 11/2012 | Ratner et al. |
| 8,333,734 B2 | 12/2012 | Zohmann |
| 8,403,911 B2 | 3/2013 | Adams et al. |
| 8,415,184 B2 | 4/2013 | Colvin et al. |
| 8,502,167 B2 | 8/2013 | Colvin, Jr. et al. |
| 8,535,537 B2 | 9/2013 | Feichtner et al. |
| 8,562,567 B2 | 10/2013 | Gundberg |
| 8,604,810 B2 | 12/2013 | Sheppard |
| 8,608,729 B2 | 12/2013 | Christenson |
| 8,608,922 B2 | 12/2013 | Papadimitrakopoulos et al. |
| 8,647,393 B2 | 2/2014 | Marshall et al. |
| 8,708,994 B2 | 4/2014 | Pettis et al. |
| 8,827,979 B2 | 9/2014 | Pesach et al. |
| 8,945,057 B2 | 2/2015 | Gym et al. |
| 8,971,981 B2 | 3/2015 | Yodfat et al. |
| 9,084,848 B2 | 7/2015 | Schiltges et al. |
| 9,114,208 B2 | 8/2015 | Smith et al. |
| 9,131,960 B2 | 9/2015 | Racz |
| 9,180,244 B2 | 11/2015 | Anderson et al. |
| 9,192,717 B2 | 11/2015 | Cote et al. |
| 9,227,013 B2 | 1/2016 | Lacy |
| 9,375,529 B2 | 6/2016 | Searle et al. |
| 9,399,094 B2 | 7/2016 | Krag et al. |
| 9,463,889 B2 | 10/2016 | Schmitz et al. |
| 9,480,792 B2 | 11/2016 | Constantineau et al. |
| 9,522,229 B2 | 12/2016 | Sonderegger et al. |
| 9,579,452 B2 | 2/2017 | Adair et al. |
| 9,713,674 B2 | 7/2017 | Carter et al. |
| 9,782,536 B2 | 10/2017 | Skutnik et al. |
| 9,782,538 B2 | 10/2017 | Cole et al. |
| 9,821,113 B2 | 11/2017 | Cole et al. |
| 9,968,742 B2 | 5/2018 | Antwerp et al. |
| 10,076,605 B2 | 9/2018 | Marbet et al. |
| 10,080,839 B2 | 9/2018 | Cole et al. |
| 10,173,007 B2 | 1/2019 | Hayter et al. |
| 10,265,483 B2 | 4/2019 | Cole et al. |
| 10,413,658 B2 | 9/2019 | Gillett et al. |
| 10,420,489 B2 | 9/2019 | Kovatchev et al. |
| 10,434,285 B2 | 10/2019 | Schoonmaker et al. |
| 10,449,296 B2 | 10/2019 | Kapas et al. |
| 10,463,787 B2 | 11/2019 | Shor et al. |
| 10,675,403 B2 | 6/2020 | Montalvo et al. |
| 10,722,653 B2 | 7/2020 | Kapas et al. |
| 10,828,418 B2 | 11/2020 | Constantineau et al. |
| 10,943,687 B2 | 3/2021 | Blomquist |
| 11,160,922 B2 | 11/2021 | Just |
| 2002/0016614 A1 | 2/2002 | Klein et al. |
| 2002/0123740 A1 | 9/2002 | Flaherty et al. |
| 2004/0075198 A1 | 4/2004 | Schweikert et al. |
| 2004/0143216 A1 | 7/2004 | Douglas et al. |
| 2004/0158207 A1 | 8/2004 | Hunn et al. |
| 2004/0236290 A1 | 11/2004 | Zimmermann |
| 2005/0137525 A1 | 6/2005 | Wang et al. |
| 2005/0192558 A1 | 9/2005 | Bernard et al. |
| 2005/0273076 A1 | 12/2005 | Beasley et al. |
| 2006/0100583 A1 | 5/2006 | Terzoli |
| 2006/0122536 A1 | 6/2006 | Haar et al. |
| 2006/0135941 A1 | 6/2006 | Porto et al. |
| 2006/0135981 A1 | 6/2006 | Lenker et al. |

(56) References Cited

U.S. PATENT DOCUMENTS

| | | |
|---|---|---|
| 2006/0211933 A1 | 9/2006 | Zimmermann et al. |
| 2007/0060834 A1 | 3/2007 | Odland et al. |
| 2007/0062251 A1 | 3/2007 | Anex |
| 2007/0282269 A1 | 12/2007 | Carter et al. |
| 2008/0091173 A1 | 4/2008 | Belley et al. |
| 2008/0108950 A1 | 5/2008 | Rioux et al. |
| 2008/0243085 A1 | 10/2008 | DeStefano |
| 2008/0269687 A1 | 10/2008 | Chong et al. |
| 2008/0287877 A1 | 11/2008 | Gresham et al. |
| 2008/0319414 A1 | 12/2008 | Yodfat et al. |
| 2009/0048563 A1 | 2/2009 | Ethelfeld et al. |
| 2009/0069750 A1 | 3/2009 | Schraga |
| 2009/0156926 A1 | 6/2009 | Messerty et al. |
| 2009/0277850 A1* | 11/2009 | Adams ............... A61M 1/3659 210/791 |
| 2010/0063445 A1 | 3/2010 | Sternberg et al. |
| 2010/0160749 A1 | 6/2010 | Gross et al. |
| 2010/0262078 A1* | 10/2010 | Blomquist ........ A61M 5/16831 73/40 |
| 2010/0286714 A1 | 11/2010 | Gym et al. |
| 2010/0298830 A1 | 11/2010 | Browne et al. |
| 2010/0303772 A1 | 12/2010 | McMillan et al. |
| 2011/0099789 A1 | 5/2011 | Ewing et al. |
| 2012/0059320 A1 | 3/2012 | Maule et al. |
| 2012/0078226 A1 | 3/2012 | Latere Dwanisa et al. |
| 2012/0265034 A1 | 10/2012 | Wisniewski et al. |
| 2013/0126349 A1 | 5/2013 | Zhang |
| 2013/0245555 A1 | 9/2013 | Dirac et al. |
| 2013/0338630 A1 | 12/2013 | Agrawal et al. |
| 2014/0025039 A1 | 1/2014 | Rajendran et al. |
| 2014/0031793 A1 | 1/2014 | Constantineau et al. |
| 2014/0058353 A1 | 2/2014 | Politis et al. |
| 2014/0088555 A1 | 3/2014 | Li et al. |
| 2015/0011970 A1 | 1/2015 | Kamen et al. |
| 2015/0051583 A1 | 2/2015 | Horvath et al. |
| 2015/0057611 A1 | 2/2015 | Bureau |
| 2015/0112302 A1 | 4/2015 | Chattaraj et al. |
| 2015/0165161 A1 | 6/2015 | Uber, III et al. |
| 2015/0182693 A1 | 7/2015 | Rosinko |
| 2015/0265767 A1 | 9/2015 | Varquez et al. |
| 2015/0283321 A1 | 10/2015 | Dang et al. |
| 2015/0290390 A1 | 10/2015 | Ring et al. |
| 2016/0095987 A1* | 4/2016 | Chattaraj ............ A61M 5/162 604/126 |
| 2016/0106919 A1 | 4/2016 | Hayter et al. |
| 2016/0279325 A1 | 9/2016 | Searle et al. |
| 2016/0290390 A1 | 10/2016 | Ambroise et al. |
| 2017/0021096 A1 | 1/2017 | Cole et al. |
| 2017/0076068 A1 | 3/2017 | Dobbles et al. |
| 2017/0189614 A1 | 7/2017 | Mazlish et al. |
| 2018/0103960 A1* | 4/2018 | Poulsen ................ A61F 2/0103 |
| 2018/0104411 A1 | 4/2018 | Chovanda et al. |
| 2018/0200412 A1 | 7/2018 | Dang et al. |
| 2018/0207356 A1 | 7/2018 | Joseph et al. |
| 2018/0220942 A1 | 8/2018 | El-Khatib et al. |
| 2018/0369479 A1 | 12/2018 | Hayler et al. |
| 2019/0053742 A1 | 2/2019 | Steil et al. |
| 2019/0054233 A1* | 2/2019 | Demaria ................ A61K 38/28 |
| 2019/0099555 A1 | 4/2019 | Patek et al. |
| 2019/0175840 A1 | 6/2019 | Schabbach et al. |
| 2019/0224409 A1 | 7/2019 | Sonderegger |
| 2019/0282753 A1 | 9/2019 | Gillett et al. |
| 2019/0388015 A1 | 12/2019 | Blomquist et al. |
| 2020/0147300 A1 | 5/2020 | Novak et al. |
| 2020/0155755 A1 | 5/2020 | Chaves et al. |
| 2020/0222625 A1 | 7/2020 | Cabiri et al. |
| 2020/0246541 A1 | 8/2020 | Neftel et al. |
| 2020/0345929 A1 | 11/2020 | Ben-David et al. |
| 2021/0016004 A1 | 1/2021 | El-Khatib et al. |
| 2021/0106803 A1 | 4/2021 | Kaiser-Pendergrast |
| 2021/0369957 A1 | 12/2021 | Wieser et al. |

FOREIGN PATENT DOCUMENTS

| | | |
|---|---|---|
| CN | 100366305 C | 2/2008 |
| CN | 101027095 B | 9/2010 |
| EP | 1608420 B1 | 11/2006 |
| EP | 2004241 B1 | 12/2008 |
| EP | 1951340 B1 | 8/2009 |
| EP | 2193814 A1 | 6/2010 |
| EP | 2457606 A1 | 5/2012 |
| EP | 2099384 B1 | 9/2018 |
| EP | 2560727 B1 | 2/2019 |
| EP | 3459574 A1 | 3/2019 |
| EP | 225462281 | 5/2019 |
| EP | 2259815 B1 | 6/2019 |
| EP | 2350895 B1 | 6/2019 |
| EP | 3656417 A1 | 5/2020 |
| EP | 3698828 A1 | 8/2020 |
| EP | 3134150 B1 | 2/2021 |
| EP | 3576823 B1 | 3/2021 |
| WO | WO96/032981 A1 | 10/1996 |
| WO | WO01/034237 A1 | 5/2001 |
| WO | WO2007/140632 A1 | 12/2007 |
| WO | WO2010/084113 A1 | 7/2010 |
| WO | 2011107988 A1 | 9/2011 |
| WO | WO2012/073097 A2 | 6/2012 |
| WO | WO2012/118762 A1 | 9/2012 |
| WO | WO2017/125817 A1 | 7/2017 |
| WO | WO2018/184012 A1 | 10/2018 |
| WO | 2019209644 A1 | 10/2019 |
| WO | WO2021/257952 A1 | 12/2021 |

OTHER PUBLICATIONS

Calthorpe, N., The history of spinal needles: getting to the point; Anaesthesia; 59(12); pp. 1231-1241; Dec. 2004.

Campolo et al., Protocols to compare infusion distribution of wound catheters; Med. Eng. Phys.; 34(3); pp. 326-332; Apr. 2012.

Centers for Disease Control and Prevention (CDCP); National Diabetes Statistics Report, 2014—Estimates of Diabetes and Its Burden in the United States; U.S. Dept. of Health and Human Services, Atlanta, GA; 8 pgs.; (year of pub sufficiently earlier than effective US filing date and any foreign priority date) 2014.

Cho et al., On-line near-infrared spectrometer to monitor urea removal in real time during hemodialysis; Appl. Spectrosc.; 62(8); pp. 866-872; Aug. 2008.

Dziubla et al., Evaluation of porous networks of poly(2-hydroxyethyl methacrylate) as interfacial drug delivery devices; Biomaterials; 22(21); pp. 2893-2899; Nov. 2001.

Edsberg et al., Insulin bolus given by sprinkler needle: effect on absorption and glycaemic response to a meal; Br. Med. J. Clin. Res. Ed.; 294(6584); pp. 1373-1376; May 30, 1987.

Jockel et al., Insulin depot formation in subcutaneous tissue; J. Diabetes Sci. Technol.; 7(1); pp. 227-237; Jan. 2013.

Miller et al., Current state of type 1 diabetes treatment in the U.S.: updated data from the T1D Exchange clinic registry; Diabetes Care; 38(6); pp. 971-978; Jun. 2015.

Neithercott, T., Infusion Sets 2014—How to choose the kind of insulin delivery that's right for you; Diabetes Forecast®; (downloaded from the internet at http://www.diabetesforecast.org/2014/Jan/infusion-sets-2014.html on Dec. 6, 2018); Dec. 2013; 2 pgs.

Patel et al., Randomized trial of infusion set function: steel versus teflon; Diabetes Technol. and Ther.; 16(1); pp. 15-19; Jan. 2014.

Pfutzner et al., Improved Insulin Absorption by Means of Standardized Injection Site Modulation Results in a Safer and More Efficient Prandial Insulin Treatment; A Review of the Existing Clinical Data; J. Diabetes Sci. Technol.; 9(1); pp. 116-122; Jan. 2015.

Walsh et al., Insulin Pump and CGM Usage in the United States and Germany: Results of a Real-World Survey with 985 Subjects; J. Diabetes Sci. Technol.; 9(5); pp. 1103-1110; Sep. 2015.

Wootten et al., Broadband 2.4 μm superluminescent GaIn—AsSb/AlGaAsSb quantum well diodes for optical sensing of biomolecules; Semicond. Sci. Technol. (Internet); 29(11); Nov. 2014 doi: 10.1088/0268-1242/29/11/115014; Avail from http://www.ncbi.nim.nih.gov/pmc/articles/PMC4283575/.

(56) References Cited

OTHER PUBLICATIONS

Coker et al., U.S. Appl. No. 17/289,009 entitled "Linear insertion device with rotational drive," filed Apr. 27, 2021.
Supplemental Partial European Search Report, Application No. 21862849.3, dated Jul. 19, 2024.

\* cited by examiner

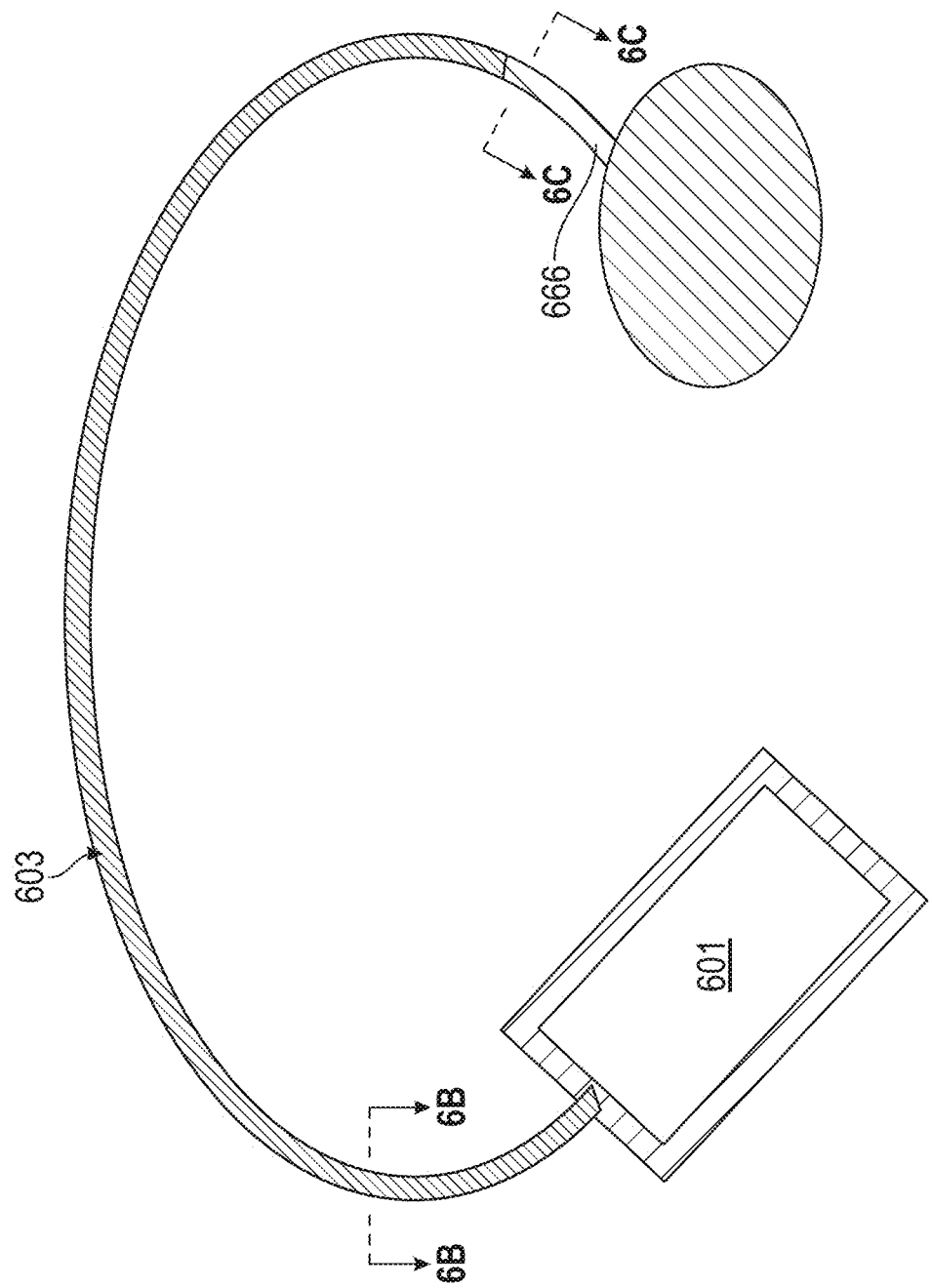

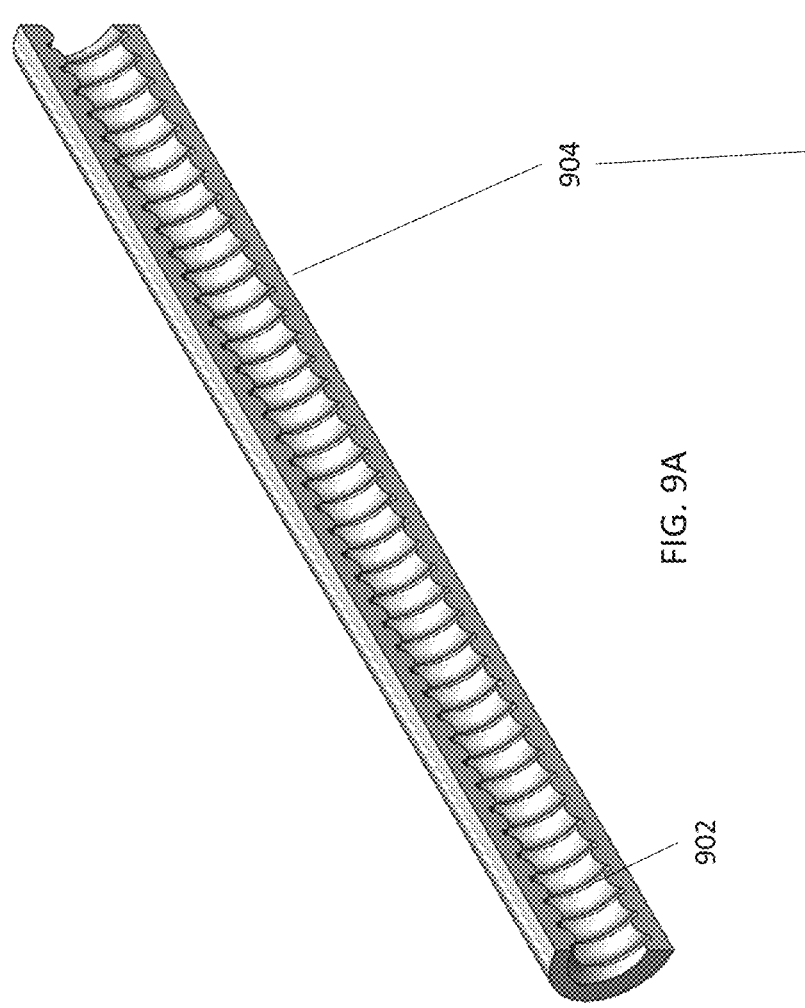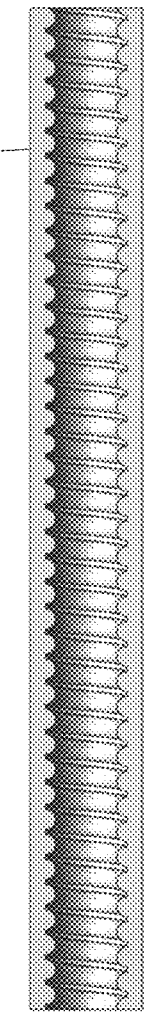

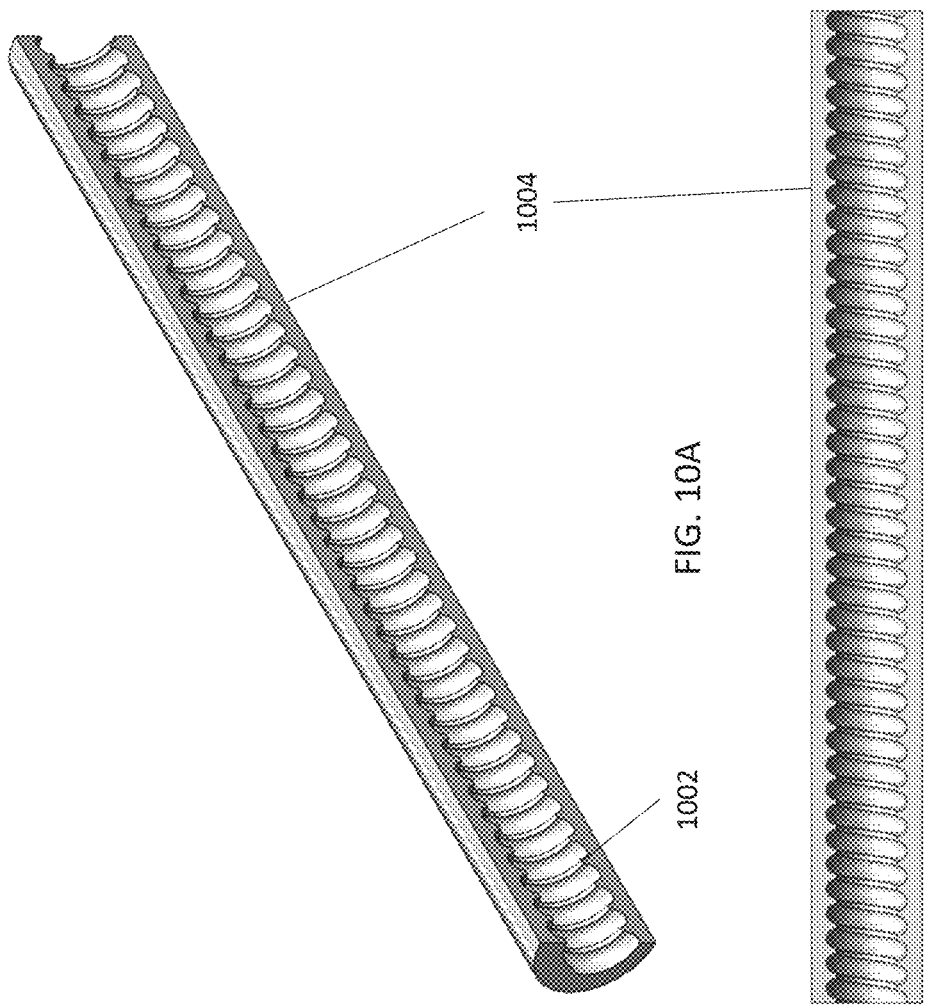

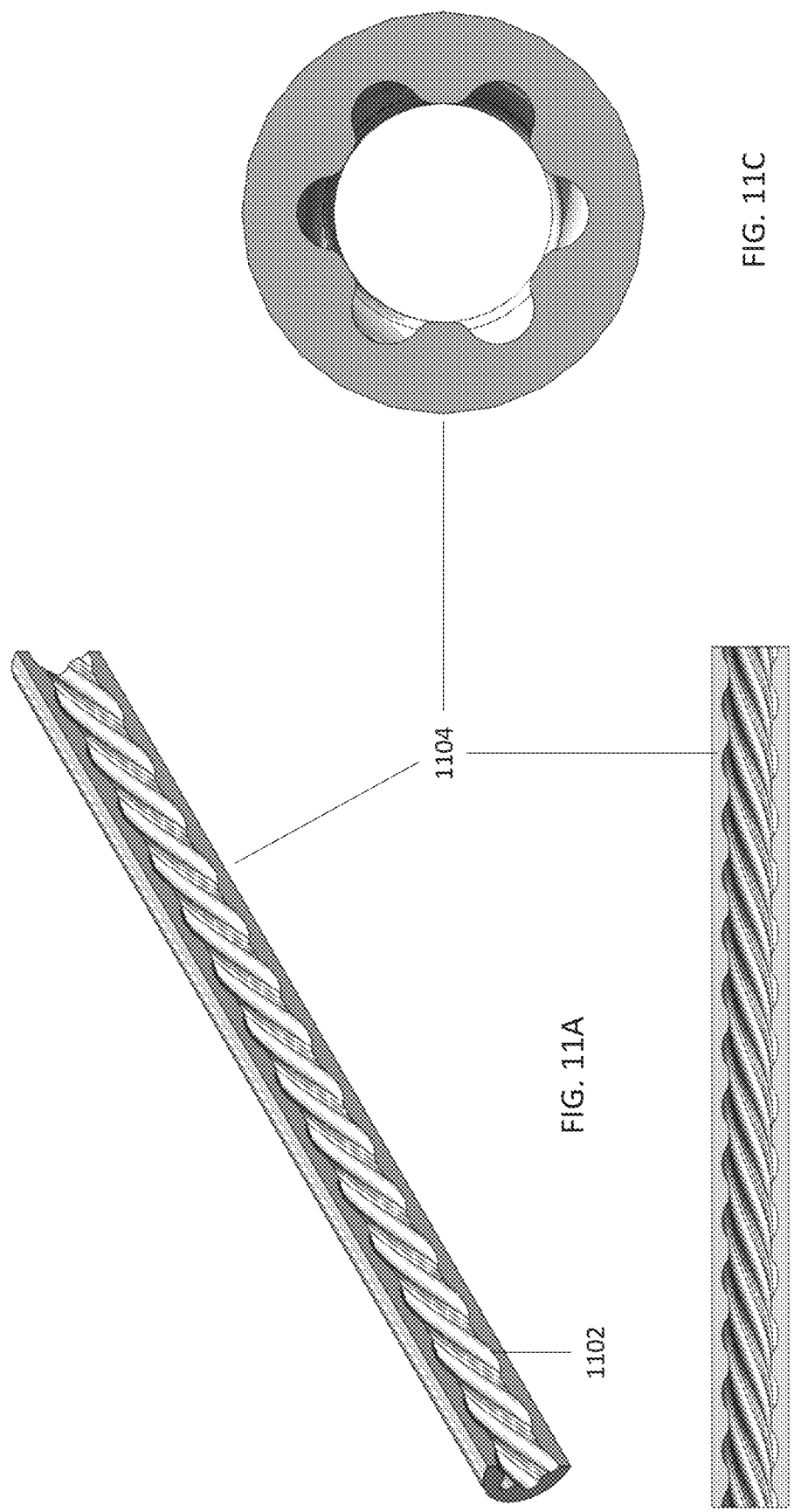

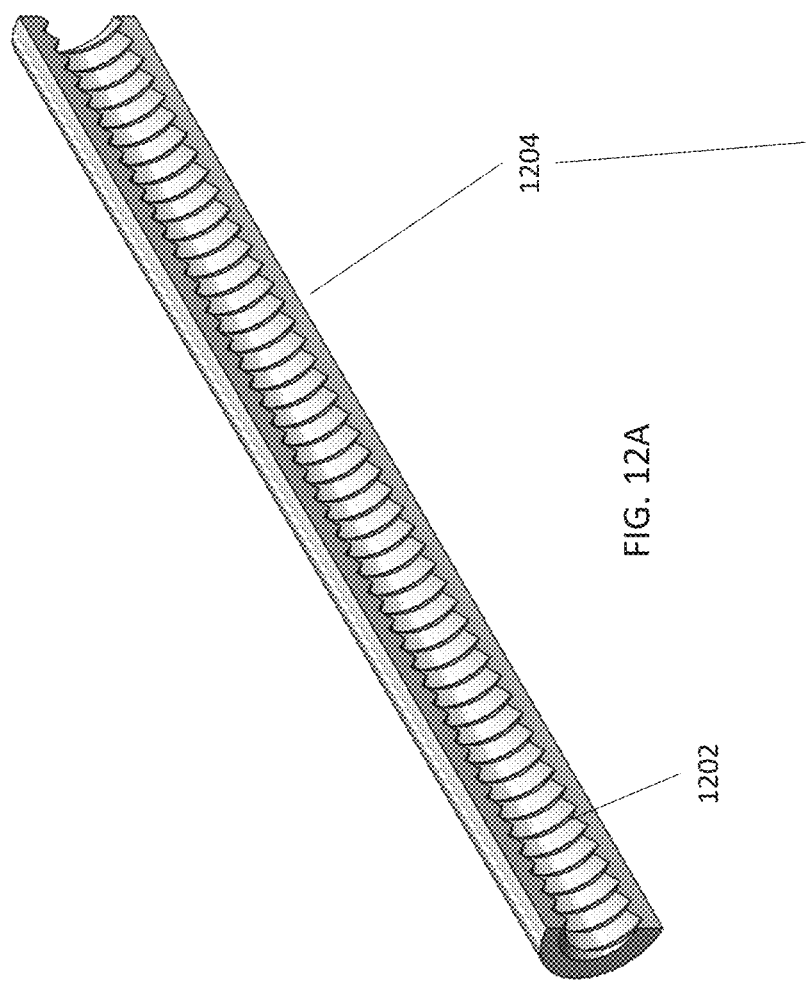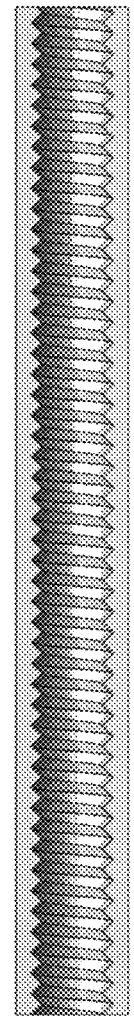

INSULIN INFUSION SET

CROSS REFERENCE TO RELATED APPLICATIONS

This application claims the benefit of U.S. Provisional Application No. 63/071,994, filed Aug. 28, 2020, which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Insulin delivery systems have become an important mechanism for treating diabetes. However, the protein insulin, including insulin analogs, is an inherently unstable molecule. In addition to chemical changes that can occur as the result general acid hydrolysis, disulfide scrambling, and other chemical transformations, insulin can be prone to self-associate and precipitate from solution under certain conditions.

To counteract this physical instability of insulin, many insulin formulations have been optimized to inhibit insulin precipitation during storage. For example, insulin formulations often include phenolic preservatives. Phenolic preservatives are important to maintain within a formulation because they induce an aggregation-resistant conformation ($R_6$) when they complex with insulin.

Preservative loss in an insulin delivery system is often a two-stage process that includes: (1) absorption of the preservative into fluid-path materials; and (2) evaporation of the fluid preservative from these materials into the air. The absorption rate is generally important in the short term, as well-chosen materials will saturate with preservative rapidly. After the material is saturated, preservative loss from drug product is driven by the rate of preservative diffusion through the material and evaporation into the surrounding environment. Because of this, preservative loss will be driven by residence time of drug product in a component, diffusion rate of preservative through materials, and material thickness.

What is needed, therefore, is an insulin delivery system that maintains insulin stability and/or prevents preservative loss prior to delivery of the insulin.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 6A-6C show an insulin delivery system with a venting element.
FIGS. 9A and 9B show various views of an embodiment of a cannula of an insulin delivery system.
FIGS. 10A-10B show various views of an embodiment of a cannula of an insulin delivery system.
FIGS. 11A-11C show various views of an embodiment of a cannula of an insulin delivery system.
FIGS. 12A and 12B show various views of an embodiment of a cannula of an insulin delivery system.

SUMMARY OF THE DISCLOSURE

Figure 1A:
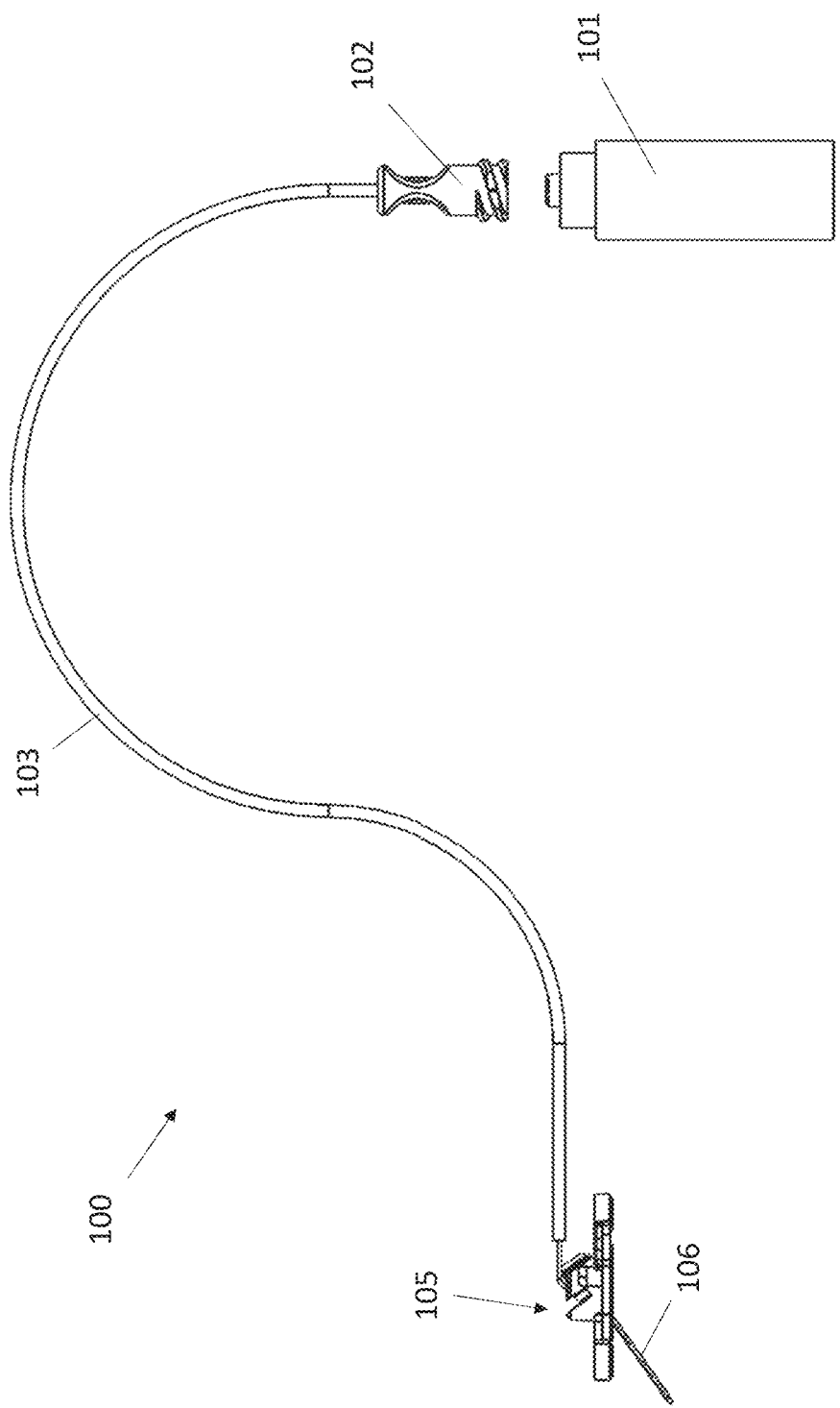
FIG. 1A shows an exemplary insulin delivery system.

In a first aspect, embodiments of an insulin delivery system are provided. The delivery system comprises a reservoir configured to hold an insulin medication therein; an infusion hub; tubing fluidically connecting the insulin reservoir and the infusion hub; a cannula configured to deliver the insulin medication to a patient; and an absorbent element positioned within the delivery system and in fluidic contact with the insulin medication, the absorbent element configured to absorb and store preservatives from the insulin medication.

In some embodiments, the system comprises an impermeable backing layer adjacent to the absorbent element and configured to maintain the preservatives within the absorbent.

The absorbent element can comprise EVOH, silicone, a low-density polymer, a PEG block-copolymer (e.g., PETG), PET, nylon, a nylon block-copolymer, a polymeric foam, or a polymeric monolith.

In some embodiments, the absorbent comprises a preservative capacity greater than a maximum concentration of preservative in the insulin medication.

The absorbent can be further configured to release preservatives to the insulin medication after storing the preservatives.

In some embodiments, the absorbent is configured to maintain the preservative concentration at the point of delivery to the patient at a concentration that minimizes local toxicity while maintaining insulin in a stable hexameric state.

The absorbent can be configured to maintain the preservative concentration at a concentration of greater than about 1.25 mg/mL. The absorbent can be configured to maintain the preservative concentration at a concentration of about 1.15-1.75 mg/mL. The absorbent can be configured to maintain the preservative concentration at a concentration of about 1.25-1.50 mg/mL.

In some embodiments, the absorbent comprises an interior layer of the tubing.

At least a portion of the insulin delivery system can be configured to prevent migration of preservatives from the insulin medication.

In some embodiments, the tubing is a multi-layer tubing, and wherein the barrier layer is at least a portion of a layer of the multi-layer tubing. The barrier layer can form an entire layer of the multi-layer tubing.

In some embodiments, the tubing comprises the barrier layer. The barrier layer can comprise a coating on the tubing. In some embodiments, the barrier layer comprises an inner layer of the tubing.

The barrier layer can comprise polyether block-amide, HDPE, polypropylene, PTFE, chloro- and fluorosilicones, hydrochloro-, hydrofluoro-, and perfluoro-polymers, chlorinated polymers (e.g., viton), metal-coated polymers (e.g., mylar), poly carbonate, organic or inorganic plasma-deposited coatings (e.g. PTFE, PVC, halogenated siloxanes, silicon suboxides), vapor-deposited coatings (such as nitrides, titanium nitride, fluorocarbons, metals), Kapton, or parylene.

In some embodiments, the system comprises a barrel connected to the cannula, and wherein the barrier layer is positioned on at least a portion of the barrel.

A connector can comprise the barrier layer.

In some embodiments, the barrier layer extends through an entire fluid path of the system.

In a further aspect, embodiments of a method of delivering insulin medication are provided. The method comprises providing a delivery system; delivering insulin medication comprising preservatives from a reservoir through tubing connecting the reservoir to an infusion hub; delivering the insulin medication to the patient through a cannula connected to the infusion hub, wherein delivering the insulin medication comprises exposing the insulin medication to an absorbent element configured to absorb and store preservatives from the insulin medication.

In some embodiments, the method comprises the absorbent element absorbing preservatives from the insulin medication.

The method can comprise the absorbent element releasing preservatives back into the insulin medication.

In some embodiments, the method comprises preventing preservative evaporation using a barrier layer on one or more components of the delivery system.

In another aspect, embodiments of an insulin delivery system are provided. The system comprises a reservoir configured to hold an insulin medication therein; an infusion hub; tubing connecting the insulin reservoir and the infusion hub; a cannula configured to deliver the insulin to a patient; and a vent in the tubing or the hub configured to release preservatives from the insulin medication prior to delivery of the insulin medication to the patient.

In some embodiments, at least a portion of the insulin delivery system includes a barrier layer configured to prevent migration of preservatives from the insulin medication.

The vent can comprise an opening in the barrier layer. In some embodiments, the vent comprises a portion of the barrier layer that is thinner than other portions of the barrier layer. The vent can comprise a portion of the barrier layer that is thinner than surrounding portions of the barrier layer.

In some embodiments, the tubing is a multi-layer tubing, and wherein the barrier layer is at least a portion of a layer of the multi-layer tubing. In some embodiments, the tubing is a multi-layer tubing, and wherein the barrier layer forms an entire layer of the multi-layer tubing.

The tubing can comprise the barrier layer. In some embodiments, the barrier layer comprises a coating on the tubing. In some embodiments, the barrier layer comprises an inner layer of the tubing.

The barrier layer can comprise polyether block-amide, HDPE, polypropylene, PTFE, chloro- and fluorosilicones, hydrochloro-, hydrofluoro-, and perfluoro-polymers, chlorinated polymers (e.g., viton), metal-coated polymers (e.g., mylar), poly carbonate, organic or inorganic plasma-deposited coatings (e.g. PTFE, PVC, halogenated siloxanes, silicon suboxides), vapor-deposited coatings (such as nitrides, titanium nitride, fluorocarbons, metals), Kapton, or parylene.

In some embodiments, the system comprises a barrel connected to the cannula, and wherein the barrier layer is positioned on at least a portion of the barrel.

In some embodiments, a connector comprises the barrier layer.

The barrier layer can extend through an entire fluid path of the system.

In some embodiments, the vent comprises EVOH, silicone, a low-density polymer, a PEG block-copolymer (e.g., PETG), PET, nylon, or a nylon block-copolymer.

In some embodiments, the vent comprises an opening in a wall or layer of the tubing or the hub.

In yet another aspect, embodiments of a method of delivering insulin are provided. The method comprises providing a delivery system; delivering insulin medication comprising preservatives from a reservoir through tubing connecting the reservoir to an infusion hub; delivering the insulin medication to the patient through a cannula connected to the infusion hub; and venting the insulin medication, thereby releasing preservatives from the insulin medication.

In some embodiments, the method comprises preventing preservative loss from the insulin medication by providing a barrier layer along at least a portion of the fluid path of the delivery system. Venting the insulin medication can comprise exposing the insulin medication to an opening in the barrier layer. In some embodiments, venting the insulin medication comprises exposing the insulin medication to a portion of the barrier layer that is thinner than other portions of the barrier layer. In some embodiments, venting the insulin medication comprises exposing the insulin medication to a portion the barrier layer that is thinner than surrounding portions of the barrier layer.

In another aspect, embodiments of an insulin delivery system are provided. The system comprises a reservoir configured to hold an insulin medication therein; an infusion hub; tubing connecting the insulin reservoir and the infusion hub; a cannula configured to deliver the insulin medication to a patient; and a filter configured to capture particulates from the insulin medication prior to delivery of the insulin to the patient.

In some embodiments, the filter comprises features internal to the cannula and in fluidic contact with the insulin configured to affect hydrodynamic flow characteristics of insulin medication flowing within the cannula and to create pressure differential regimes to promote the capture and retention of aggregate particles that have formed out of solution.

The features can repeat along at least a portion of a length of the cannula.

In some embodiments, a ratio of a width of the features and a period of the features is greater than about 1:1 and less than about 1:4.

In some embodiments, the features comprise internally molded features within the cannula. In some embodiments, the features comprise internally extruded features within the cannula.

The internal features can comprise polyether block-amide.

In some embodiments, the filter comprises an internal coil within the cannula.

The internal coil can comprise a round wire. The internal wire can comprise a flat wire.

In some embodiments, the internal coil comprises an engineering polymer. In some embodiments, the internal coil comprises stainless steel.

In some embodiments, the filter comprises a structural component to prevent crushing or kinking of the extruded cannula.

The filter can comprise a threaded inner surface of the cannula.

The threaded surface can comprise angular or pointed threads. The threaded surface can comprise flat threads.

The threaded surface can comprise angled, overlapping, or buttress style threads.

In some embodiments, at least a portion of the insulin delivery system includes a barrier layer configured to prevent migration of preservatives from the insulin medication.

The tubing can be a multi-layer tubing, and the barrier layer can be at least a portion of the multi-layer tubing. The tubing can be a multi-layer tubing, and the barrier layer can form an entire layer of the multi-layer tubing.

In some embodiments, the tubing comprises the barrier layer. The barrier layer can comprise a coating on the tubing. The barrier layer can comprise an inner layer of the tubing.

In some embodiments, the barrier layer comprises polyether block-amide, HDPE, polypropylene, PTFE, chloro- and fluorosilicones, hydrochloro-, hydrofluoro-, and perfluoro-polymers, chlorinated polymers (e.g., viton), metal-coated polymers (e.g., mylar), poly carbonate, organic or inorganic plasma-deposited coatings (e.g. PTFE, PVC, halogenated siloxanes, silicon suboxides), vapor-deposited coatings (such as nitrides, titanium nitride, fluorocarbons, metals), Kapton, or parylene.

The system can comprise a barrel connected to the cannula, and the barrier layer can be positioned on at least a portion of the barrel.

A connector can comprise the barrier layer.

In some embodiments, the barrier layer extends through an entire fluid path of the system. The system can comprise a vent in the tubing or the hub configured to release preservatives from the insulin medication prior to delivery of the insulin medication to the patient.

In some embodiments, at least a portion of the insulin delivery system includes a barrier layer configured to prevent migration of preservatives from the insulin medication and wherein the vent comprises an opening in the barrier layer. In some embodiments, at least a portion of the insulin delivery system includes a barrier layer configured to prevent migration of preservatives from the insulin medication and wherein the vent comprises a portion of the barrier layer that is thinner than other portions of the barrier layer. In some embodiments, at least a portion of the insulin delivery system includes a barrier layer configured to prevent migration of preservatives from the insulin medication and wherein the vent comprises a portion of the barrier layer that is thinner than surrounding portions of the barrier layer.

The system can further comprise an absorbent element positioned within the delivery system and in fluidic contact with the insulin medication, the absorbent element configured to absorb and store preservatives from the insulin medication.

The system can comprise an impermeable backing layer adjacent to the absorbent element and configured to maintain the preservatives within the absorbent.

In some embodiments, the absorbent element comprises EVOH, silicone, a low-density polymer, a PEG block-copolymer (e.g., PETG), PET, nylon, a nylon block-copolymer, a polymeric foam, or a polymeric monolith.

The absorbent can comprise a preservative capacity greater than a maximum concentration of preservative in the insulin medication.

In some embodiments, the absorbent is further configured to release preservatives to the insulin medication after storing the preservatives.

The absorbent can be configured to maintain the preservative concentration at the point of delivery to the patient at a concentration that minimizes local toxicity while maintaining insulin in a stable hexameric state.

The absorbent can comprise an interior layer of the tubing.

In still a further aspect, embodiments of a method for delivering insulin are provided. The method comprises providing a delivery system; delivering insulin medication comprising preservatives from a reservoir through tubing connecting the reservoir to an infusion hub; filtering the insulin medication to capture particulates from the insulin medication prior to delivery of the insulin medication to the patient; and delivering the insulin medication to the patient through a cannula connected to the infusion hub.

In some embodiments, the method comprises affecting hydrodynamic flow characteristics of insulin medication flowing within the cannula and creating differential pressure regimes to promote the capture and retention of aggregate particles that have formed out of solution.

Filtering the insulin medication can comprise providing, within a flow path of the insulin medication, features internal to the cannula, thereby affecting hydrodynamic flow characteristics of insulin medication flowing within the cannula and creating differential pressure regimes to promote the capture and retention of aggregate particles that have formed out of solution.

Filtering the insulin medication can comprise using internally molded features within the cannula. Filtering the insulin medication can comprise using internally extruded features within the cannula.

In some embodiments, filtering the insulin medication comprises using a coil internal to the cannula, the coil configured to create a region of features affecting hydrodynamic flow characteristics of insulin medication flowing within the cannula and creating differential pressure regimes to promote the capture and retention of aggregate particles that have formed out of solution.

The coil can comprise a round wire. The coil can comprise a flat wire.

The coil can comprise stainless steel. The coil can comprise an engineering polymer.

The method can further comprise exposing the insulin medication to an absorbent element configured to store preservatives from the insulin medication.

In some embodiments, the method comprises the absorbent element absorbing preservatives from the insulin medication.

The method can comprise the absorbent element releasing preservatives back into the insulin medication.

In some embodiments, the method comprises preventing preservative evaporation using a barrier layer on one or more components of the delivery system.

The method can comprise venting the insulin medication, thereby releasing preservatives from the insulin medication.

In some embodiments, the method comprises preventing preservative loss from the insulin medication by providing a barrier layer along at least a portion of the fluid path of the delivery system, and wherein venting the insulin medication comprises exposing the insulin medication to an opening in the barrier layer. In some embodiments, the method comprises preventing preservative loss from the insulin medication by providing a barrier layer along at least a portion of the fluid path of the delivery system, and wherein venting the insulin medication comprises exposing the insulin medication to a portion of the barrier layer that is thinner than other portions of the barrier layer. In some embodiments, the method comprises preventing preservative loss from the insulin medication by providing a barrier layer along at least a portion of the fluid path of the delivery system, and wherein venting the insulin medication comprises exposing the insulin medication to a portion of the barrier layer that is thinner than surrounding portions of the barrier layer.

In another aspect, embodiments of an insulin delivery system are provided. The system comprises a reservoir configured to hold an insulin medication therein; an infusion hub; tubing fluidically connecting the insulin reservoir and the infusion hub; and a cannula configured to deliver the insulin medication to a patient; wherein at least a portion of the insulin delivery system includes a barrier layer configured to prevent migration of preservatives from the insulin medication.

In some embodiments, the tubing is a multi-layer tubing, and wherein the barrier layer is a layer of the multi-layer tubing.

The barrier layer can comprise polyether block-amide, HDPE, polypropylene, PTFE, chloro- and fluorosilicones, hydrochloro-, hydrofluoro-, and perfluoro-polymers, chlorinated polymers (e.g., viton), metal-coated polymers (e.g., mylar), poly carbonate, organic or inorganic plasma-deposited coatings (e.g. PTFE, PVC, halogenated siloxanes, silicon suboxides), vapor-deposited coatings (such as nitrides, titanium nitride, fluorocarbons, metals), Kapton, or parylene.

DETAILED DESCRIPTION

Figure 1B:
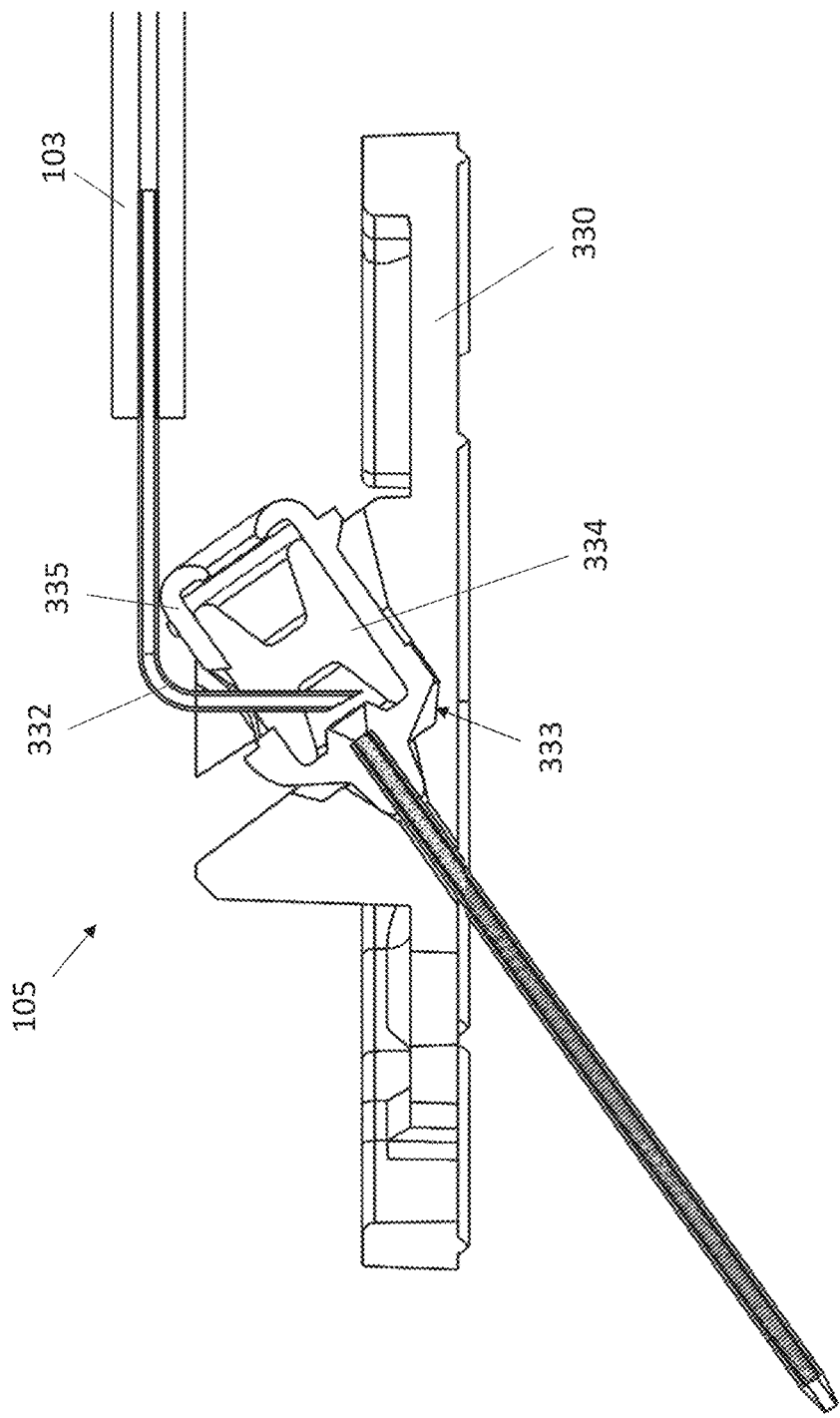
FIG. 1B shows a close-up of the hub of the delivery system of FIG. 1A.

Referring to FIG. 1A, an insulin delivery system 100 includes an insulin reservoir 101 (configured to store an insulin medication therein), a reservoir-set connector 102, tubing 103, a hub 105, and an infusion cannula 106. As shown in FIG. 1B, the hub 105 can include a patch 330 or other mechanism configured to adhere to the patient, a barrel 333 connected to the cannula 106, and an introducer 332 extending from the tubing 103. The barrel 333 can include a mechanical housing 335 configured to house a septum. The fluid introducer 332 can be configured to pierce the septum 334 and to deliver fluid to the cannula 106. The fluid path for the insulin medication, therefore, can run from the reservoir 101 through the tubing 103 to the barrel 333 and to the patient via the cannula 106.

In some embodiments, some or all of the fluid path can include a barrier therein to inhibit preservative evaporation and/or loss. The barrier can be, for example, a coating or layer positioned along the fluid path. In other embodiments, the barrier can be the entire component (e.g., the entire the set-cannula connector 105). In some embodiments, each component can have a different barrier.

Figure 2:
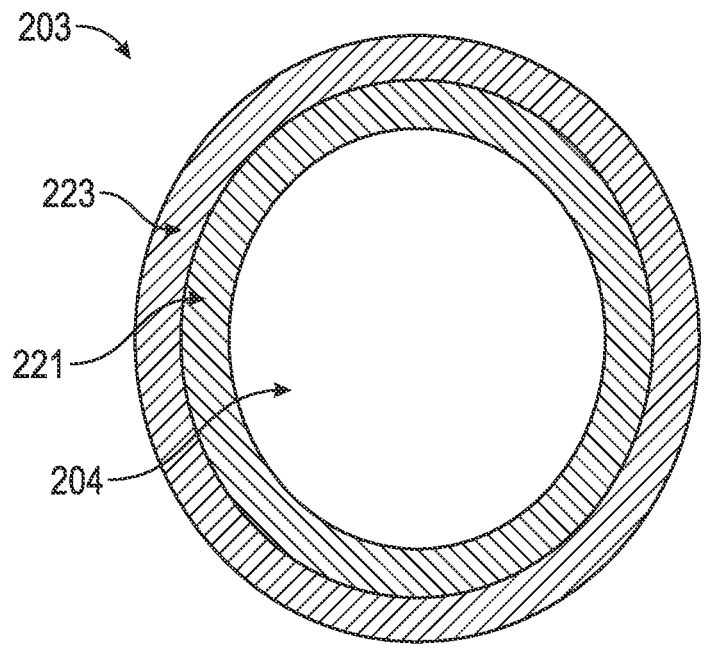
FIG. 2 shows a cross-section of multi-layer tubing of an insulin delivery system where one layer is a barrier layer.

For example, referring to FIG. 2, the tubing 203 can be a multi-layer tubing, wherein the fluid path 204 is surrounded by a barrier 221 configured to prevent preservative loss and an outer layer 223 configured to provide mechanical protection and/or bond to other components of the system.

Figure 3:
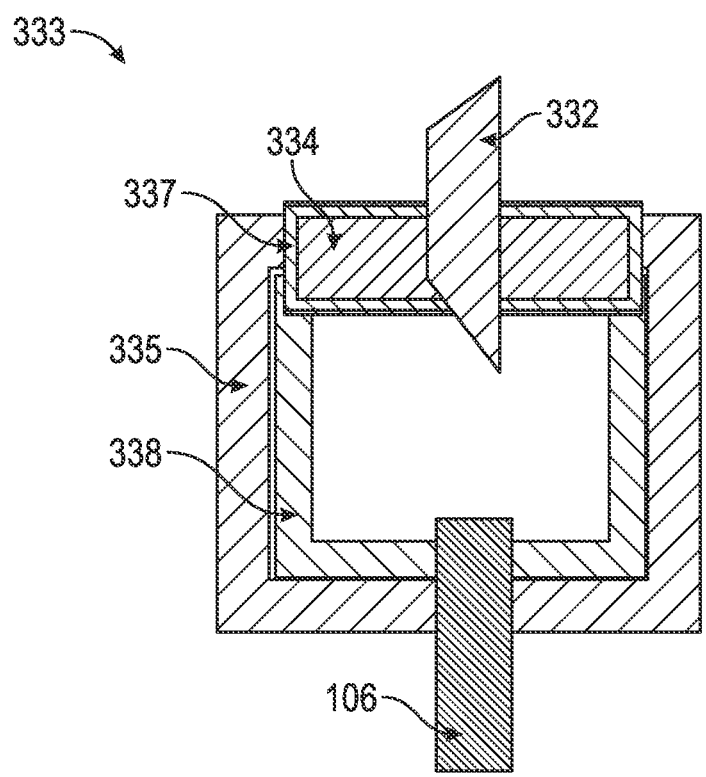
FIG. 3 shows a cross-section of a barrel of an insulin delivery system where the housing has a barrier layer therein.
Figure 8:
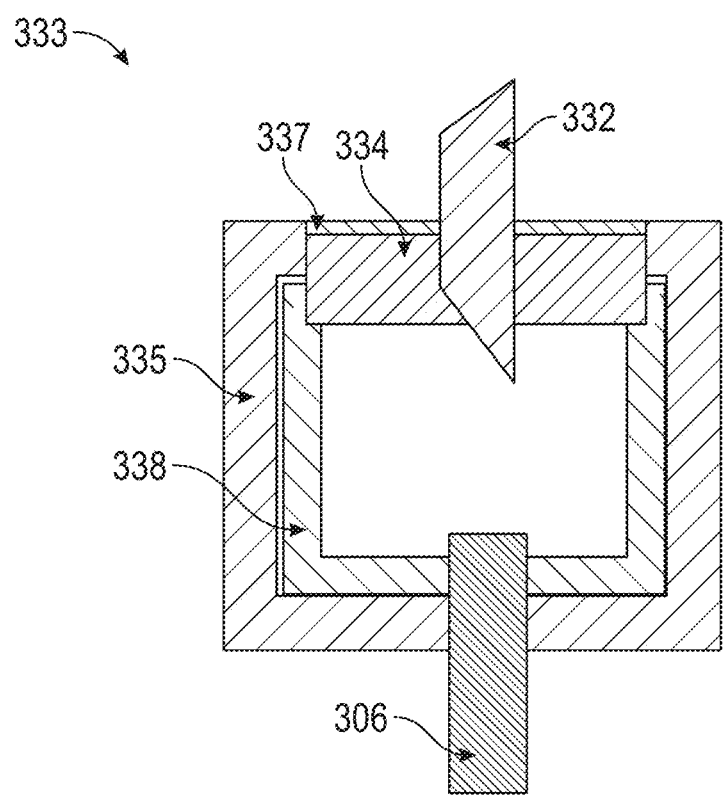
FIG. 8 shows a cross-section of a barrel of an insulin delivery system where the septum has a barrier layer thereon.

As another example, referring to FIG. 3, the septum 334 can be coated with a barrier 337 to minimize preservative loss and/or the interior of the mechanical housing 335 can be lined with a barrier 338 to minimize preservative loss. In some embodiments, shown in FIG. 8, the barrier 337 can be on only one side of the septum 334.

In embodiments where the barrier extends along multiple components, the barrier can be discrete or continuous. Similarly, the barrier can have different characteristics (e.g., be made of different materials) from component to component or can be the same from component to component.

The barriers described herein can include, for example, polyether block-amide, HDPE, polypropylene, PTFE, chloro- and fluorosilicones, hydrochloro-, hydrofluoro-, and perfluoro-polymers, chlorinated polymers (e.g. viton), metal-coated polymers (e.g., mylar), poly carbonate, organic or inorganic plasma-deposited coatings (e.g. PTFE, PVC, halogenated siloxanes, silicon suboxides), vapor-deposited coatings (such as nitrides, titanium nitride, fluorocarbons, metals), Kapton, or parylene.

In some specific examples, a length of the tubing 332 within the barrel 333 can prevent preservative evaporation. The outer housing 335 of the barrel 333 can also serve as a barrier if some of the internal fluid-contacting components need to be made from specific materials because of their physical/mechanical properties. In another embodiment, a connector (e.g., connector 102) that includes a fluid path may be fabricated from ceramic, or polytetrafluoroethylene or another a material with low permeability to preservative. In another embodiment, a barrier layer may form a continuous path that extends through more than one component in the system, such as a tube that originates at the connector 102 and extends through the tubing 332, the hub 105, and ends with a direct connection to the cannula 106.

In some embodiments, the fluid path can include a ballast therein. The ballast can be an absorbent material configured to absorb and release preservatives from the insulin medication. The ballast can advantageously be configured to absorb preservatives from the insulin medication when there is a high preservative concentration (e.g., when the insulin medication moves quickly during bolus delivery or priming) and to release preservatives into to the insulin medication when the preservative concentration is low (e.g., when the drug product moves slowly during basal delivery or when delivery is suspended or stopped).

The ballast can help maintain the preservative concentration at the point of delivery to the patient at a concentration that minimizes local toxicity while maintaining insulin in a stable hexameric state. In some embodiments this concentration can be about greater than 1.25 mg/mL (or 1.25-1.50 mg/mL or 1.15-1.75 mg/mL, etc.). The ballast can thus create a "smoothed" preservative concentration vs. time profile, which can advantageously provide: (1) a consistent pharmacokinetic profile resulting from consistent preservative concentration at the point of delivery because preservative absorption into tissue is a step that must occur before insulin can be absorbed; and (2) a decrease in the incidence of site loss because maintaining preservative concentration above the threshold needed for insulin stability will reduce the amount of insulin aggregates introduced at the infusion site.

Figure 4:
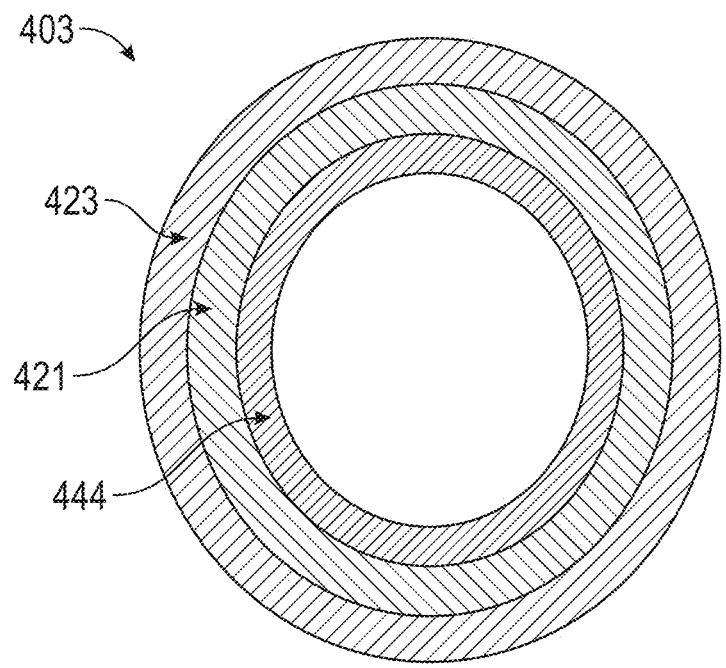
FIG. 4 shows a cross-section of multi-layer tubing of an insulin delivery system where one layer is a ballast.

For example, referring to FIG. 4, a ballast 444 can form an interior layer of the tubing 403. The ballast 444 can be bordered by a barrier 421 to prevent the preservatives from leaving the ballast 444. Outer layer 423 can surround the barrier 421, similar to as described with respect to tubing 203.

Figure 5:
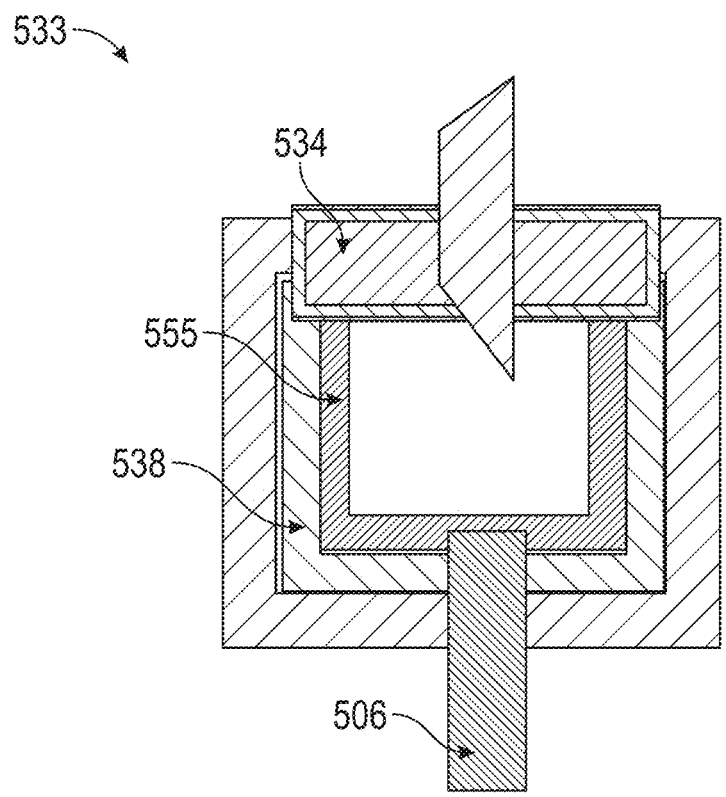
FIG. 5 shows a cross-section of a barrel of an insulin delivery system where the housing further has a ballast therein.

As another example, referring to FIG. 5, a ballast 555 can form an interior layer of the housing 335 of a barrel 533. A barrier layer 538 can border the ballast 555 to prevent the preservatives from leaving the ballast 555.

The ballast(s) can advantageously be configured to maintain a consistent preservative concentration at the point of delivery (e.g., from the cannula 506 to the patient) by acting as a damper or sink for preservative concentration. The ballast can advantageously counteract the effects of insulin medication passing through portions of the fluid path (e.g., the septum 534) where preservative evaporation cannot be prevented.

The ballast can advantageously work in the following non-limiting manner.

The preservative concentration of any given unit of insulin delivered by a continuous subcutaneous insulin infusion set (e.g., the infusion delivery system described herein) is a function of the residence time of that unit within the fluid path components were preservative evaporation occurs. When a bolus is delivered, the residence time of the fluid is short—and hence preservative loss is small and preservative concentration remains near the initial level. When the system is delivering at basal rates of when delivery is temporarily stopped, the residence time of a unit of insulin medication is longer, and therefore there is more time for preservative to be lost by diffusion/evaporation at one or more elements within the fluid path.

In some embodiments, the priming process can serve to charge the ballast. When the insulin delivery system is primed (e.g., prior to use), the insulin medication moving through the system can have the minimum possible residence time, and therefore the highest possible preservative concentration. If a preservative ballast is in this fluid path, it can absorb some of the preservative from the initial bolus. This can load the ballast up with preservative. In some embodiments, the effect can be to reduce the initial concentration of preservative and possibly reduce the toxicity of the initial fluid delivered to the patient by reducing the initial preservative exposure.

Additionally, bolus delivery is much faster than basal and can be as fast as priming. Accordingly, bolus delivery can offer another opportunity to charge the ballast (similar to as described with respect to priming).

During basal delivery or when delivery is stopped temporarily, the ballast can return preservative to the insulin flowing past. In the case of basal insulin delivery, the insulin reaching the point of delivery is generally preservative-depleted. This situation is the hardest on delivered insulin because (1) the preservative stabilization effect is at its lowest and (2) the insulin spends the most time in a preservative-depleted environment where aggregation is most favored. The ballast can advantageously release preservative into preservative-depleted drug product that passes by. This can increase the insulin stabilization. In some embodiments, the preservative ballast can be positioned directly downstream of any known point of preservative loss, such as just downstream of turns or angles in the fluid path or areas where the infusion set tubing does not adequately prevent preservative loss.

The ballast can be made of a material that enables preservative to diffuse rapidly, but does not cause the preservative to be sequestered irreversibly. Exemplary materials for the ballast include polymers with highly disordered domains or materials with aromatic groups that can act to solvate preservative molecules within the preservative matrix. For example, the ballast can be made of EVOH, silicone, a low-density polymer, a PEG block-copolymer (e.g., PETG), PET, nylon, a nylon block-copolymer, polyurethane, or polyurethane copolymers.

Example 1

Approximately 0.5 g of four different candidate materials were chopped into small pieces with edges generally no larger than about 4 mm$^2$ with a clean razor. The material was transferred into a clean, tared 4 mL vial and weighed to determine the actual mass of material. Each vial was filled with 3 mL of 20 mg/mL m-cresol solution, sealed, and agitated at ambient temperature for 2 hours. At the end of this time, the m-cresol solution was decanted and each solid was quickly washed 3 times with 2 mL DI water (<5 sec per wash with mixing). After the final wash, residual water was decanted to the greatest extent possible. Finally, each material sample was covered with fresh DI water and left static at room temperature for 1 hour. (Note that the residence time of insulin U100 within an infusion set can be up to 8 hours.) The resulting solutions were decanted and transferred into tared HPLC vials. The mass of each extract solution was determined. 85% recovery of the extraction fluid was assumed for calculations. The amount of m-cresol in each extract was determined with HPLC. The results are provided in Table 1, below:

TABLE 1

| Material | [m-cresol] mg/g | Mass Solid | Mass Water | Approx. Cap. = mg/g |
| --- | --- | --- | --- | --- |
| Pebax 7233 | 3.16 | 469 | 665 | 5.27 |
| Pebax 6333 | 2.41 | 447 | 740 | 4.70 |
| Silibione 4745 | 3.13 | 446 | 875 | 7.23 |
| Silibione 4747 | 4.34 | 442 | 625 | 7.22 |

These results show that the preservative capacity of all these materials exceeds the maximum preservative concentration in the most common rapid-acting insulin U-100 products used for CSII therapy, such as 3.22 mg/mL total for insulin aspart products (e.g., Novolog, Fiasp) and 3.15 mg/mL total for insulin lispro products (e.g. Humalog, Lyumjev, Admelog).

Incubation of an excess of fluid with each material brought the preservative concentration from zero up to a level above the minimum required (≥1.15 mg/mL) to maintain antimicrobial effectiveness in insulin U-100 drug products.

It will be appreciated that the embodiments of ballasts described herein are not limited to those embodiments described in Example 1.

Figure 6C:
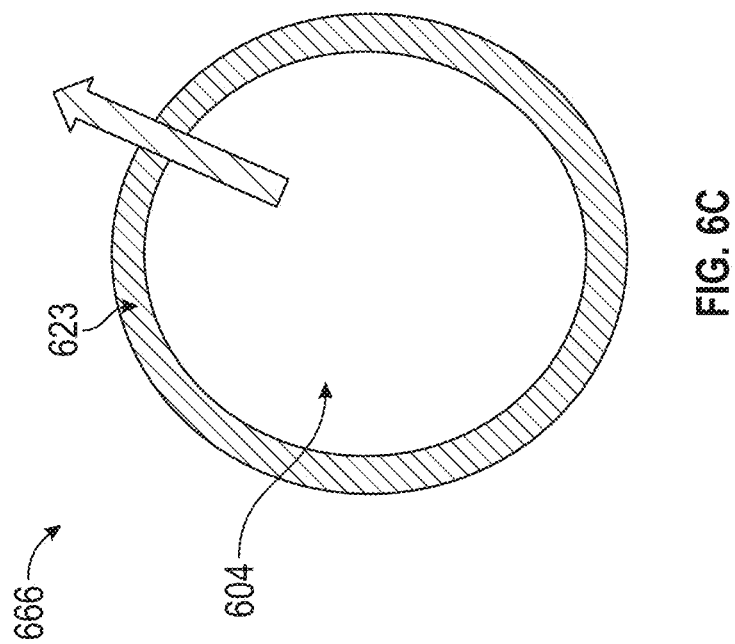
Figure 6B:
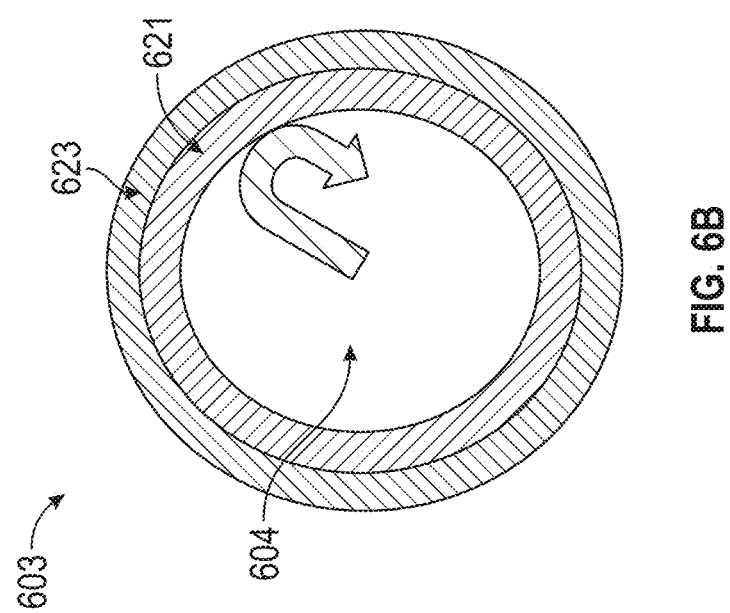

In some embodiments, the insulin delivery system can include a venting element therein configured to release excess preservatives just prior to delivery of insulin to the patient (e.g., so as to reduce inflammation or other reaction in the patient due to the inherent toxicity of the preservatives). For example, referring to FIGS. 6A-6C, the insulin delivery system can include a barrier 621 radially inwards of the outer wall 623 of the tubing 603. The barrier 621 can end, however, at a vent 666 that is adjacent and/or proximate to the hub. The vent 666 can thus be positioned along the fluid path 604 from the reservoir 601 just prior to delivery of insulin to the patient. As shown by the arrow in FIG. 6B, the barrier 621 can prevent preservative from leaving the fluid path 604. However, as shown by the arrow in FIG. 6C, the vent 666 (i.e., portion without the barrier 621) can allow the preservative to leave the fluid path 604. The vent 666 can thus allow preservative to exit the system prior to being delivered to the patient.

In some embodiments, the vent 666 can be an opening (e.g., an annular opening). In other embodiments, the vent 666 can include a thinning in the barrier, a material with lower barrier properties, a perforation of the barrier, or a material that has a high degree of preservative attraction in contact with the fluid path and the exterior environment. In some embodiments, for example, the vent 666 can be made of EVOH, silicone, a low-density polymer, a PEG block-copolymer (e.g., PETG), PET, nylon, or a nylon block-copolymer.

In some embodiments, the vent 666 can be positioned inside the hub rather than proximal or adjacent to the hub.

In some embodiments, the insulin delivery system described herein can include a filter configured to capture particulates (e.g., aggregated insulins or lubricating oils) from the insulin prior to delivery to the patient.

In some embodiments the filter can comprise features internal to at least a portion of the delivery system (e.g., the cannula) that affect hydrodynamic flow characteristics of insulin medication flowing within the cannula and create differential pressure regimes to promote the capture and retention of aggregate particles that have formed out of solution.

In some embodiments, the internal features comprise repeating mechanical features that are configured to form differential pressure regimes within the flow of the medication. The mechanical features may comprise angular features, undulations, features with both angular and curved portions, etc.

In some embodiments, the spacing between the repeating features is configured to promote differential pressure regimes. The ratio of the width of each feature and the spacing between the repeating mechanical features can be about 1:1 to about 1:5 (or 1:1 to 1:2, or 1:1 to 1:3, or 1:1 to 1:4, or 1:1 to 1:6 or more, etc.).

In some embodiments, the internal features are formed through molding or extrusion (e.g., threads). Such features can provide a manufacturing advantage over, for example, a separate structure (e.g., coil) added to infusion set components as such features can be more inexpensive and easier to manufacture. Internal features formed through molding or extrusion also can provide sufficient column strength to a component such as a cannula to allow for insertion. Internal features formed through molding or extrusion can also provide sufficient modulus strength to the component while still providing enough flexibility to avoid tissue disruption.

In some embodiments, the internal features comprise polyether block-amide.

In some embodiments, the internal features are formed integrally with the infusion set components (e.g., cannula). In some embodiments, the internal features are separate components that are added to the infusion set components.

Figure 7:
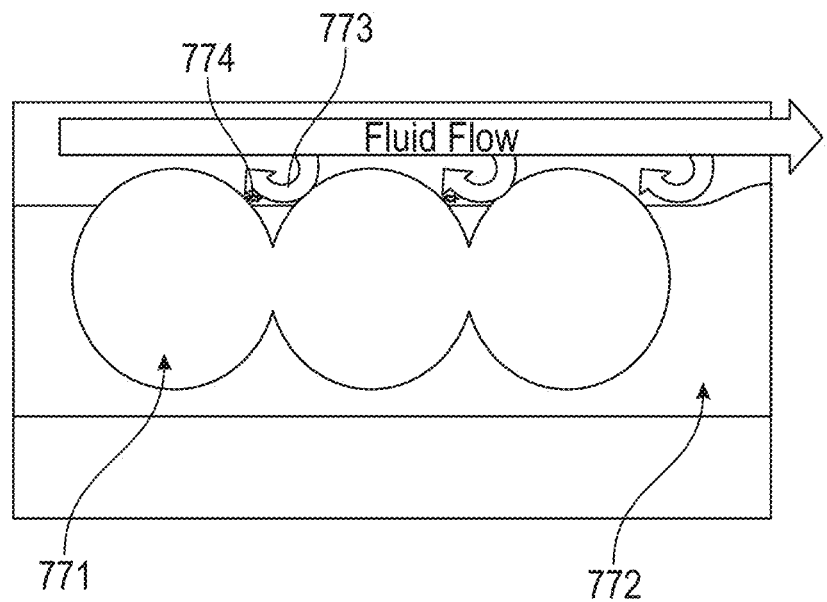
FIG. 7 shows a particulate trap.

Referring to FIG. 7, a particulate trap in the cannula (e.g., along the length of an inner wall of the cannula) can include a metal coil 771 therein designed to provide mechanical flow resistance zones and cavities on the fluid-path periphery where large molecular assemblies (aggregates) become trapped while smaller molecules, such as insulin hexamers can diffuse back into the moving fluid.

The coil can comprise stainless steel or an engineering polymer.

The coil can comprise a round wire or a flat wire.

In some embodiments, the coil can be tightly wound with a pitch of 1:1 thereby creating a proliferation of differential pressure areas along the wall of the lumen created by the coil.

In other embodiments, the coil can be tightly wound with a pitch greater than 1:1 such as 1:2, 1:3 etc. thereby creating an extended differential pressure areas along the wall of the lumen created by the coil.

In some embodiments, the trap in the cannula can also include a high-friction inner tubing surface 772, where the surface finish can be controlled to have cavities that create small eddies 773 in the flow where large molecules 774 become trapped, but small molecules can diffuse out.

In some embodiments, the filter comprises a threaded or similar surface within a portion of the delivery system or infusion set (e.g., the cannula). Any thread or other surface pattern that provides a series of repeating mechanical structures that promote differential pressure regimes within the flow path can be used.

The threaded inner surface may be formed via molding or extrusion.

The threaded inner surface may be formed integrally with the infusion or delivery component (e.g., cannula).

The threads may comprise sharp or pointed edges. In some embodiments, the threads comprise flat or square edges.

The threads may comprise a thread angle of about 0°-30°.

For example, in some embodiments, filter comprises a threaded surface 902 within the cannula 904 as shown in the perspective and side sectional views of FIGS. 9A and 9B. The threads may comprise angular, sharp, or pointed edges, as shown in FIG. 9A.

As described above, in some embodiments, the filter comprises a threaded surface 1002 within the cannula 1004, as shown in the perspective and side sectional views of FIGS. 10A and 10B. The threads may comprise flat edges. Such flat edges create increased differential pressure along the flat surface and thereby create increased negative pressure in the areas of the minor thread diameter (root).

Figure 15B:
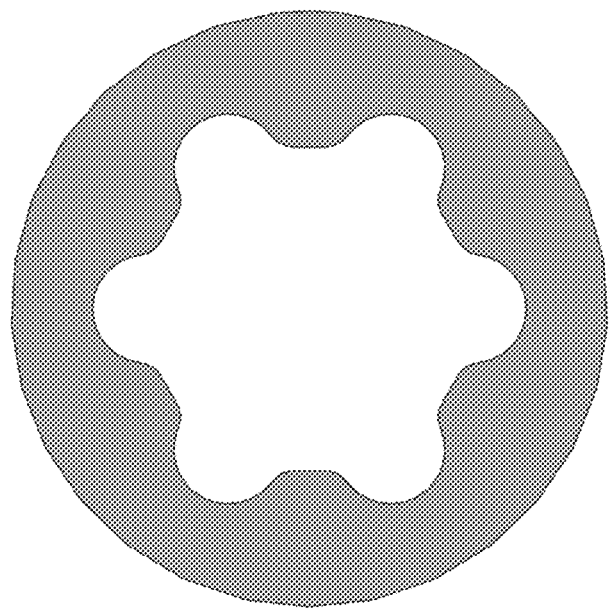
FIGS. 15A and 15B show embodiments of a cannula of an insulin delivery system.
Figure 15A:
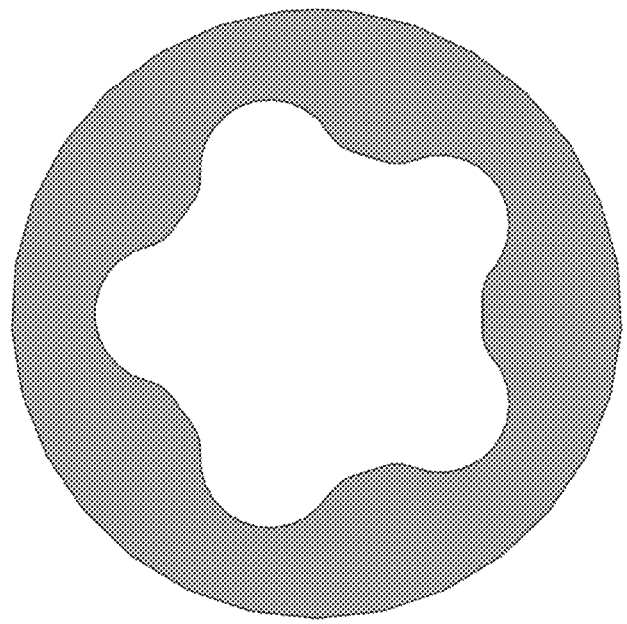

In some embodiments, the filter comprises a threaded surface 1102 within the cannula 1104 comprising a larger thread angle, as shown in the perspective and side sectional views of FIGS. 11A and 11B. For example, the thread angle can be about 30-75° (or about between 0-90°, 20-80°, 35-70°, 45-65°, etc.). A greater angle of the repeating structures (e.g., thread angle) can reduce the frequency of the repeating mechanical structure along the flow path of the medication. In certain such embodiments, the component may comprise a greater number of repeating angles, undulations, or other features affecting hydrodynamic flow characteristics of insulin medication flowing within the cannula and creating differential pressure regimes along a circumferential dimension, as shown in the end view of FIG. 11C. FIGS. 15A and 15B show other embodiments of a cannula with features affecting hydrodynamic flow characteristics of insulin medication flowing within the cannula and creating differential pressure regimes along a circumferential dimension of a cannula.

In some embodiments, the filter comprises a threaded surface 1202 within the cannula 1204, as shown in the perspective and side sectional views of FIGS. 12A and 12B. The threads may comprise angled, overlapping, or buttress style threads.

Example 2

Figure 13:
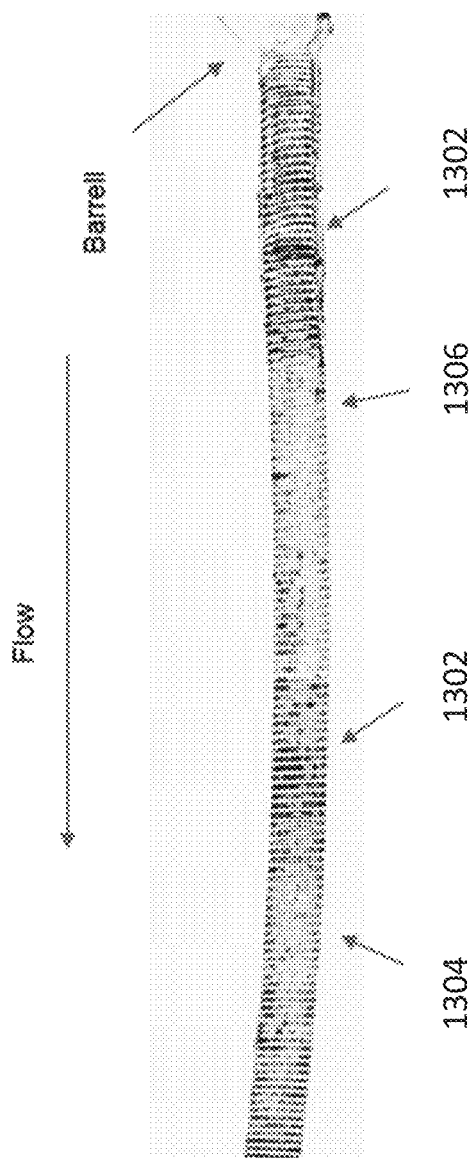
FIG. 13 shows a false-color fluorescence image of an embodiment of an infusion set.

A clinical infusion set was flushed with Thioflavin-t solution. FIG. 13 shows a false-color fluorescence image of the infusion set. Black areas 1302 indicate fluorescence, and white areas 1304 show non-fluorescence. The infusion set comprises a stainless steel coil, visible as white stripes running the length of the infusion set 1306 (e.g., cannula). The black stripes show the insulin aggregates. This image demonstrates the efficacy of using a filter, as described herein to filter out aggregate particles from delivered medication.

Example 3

Figure 14:
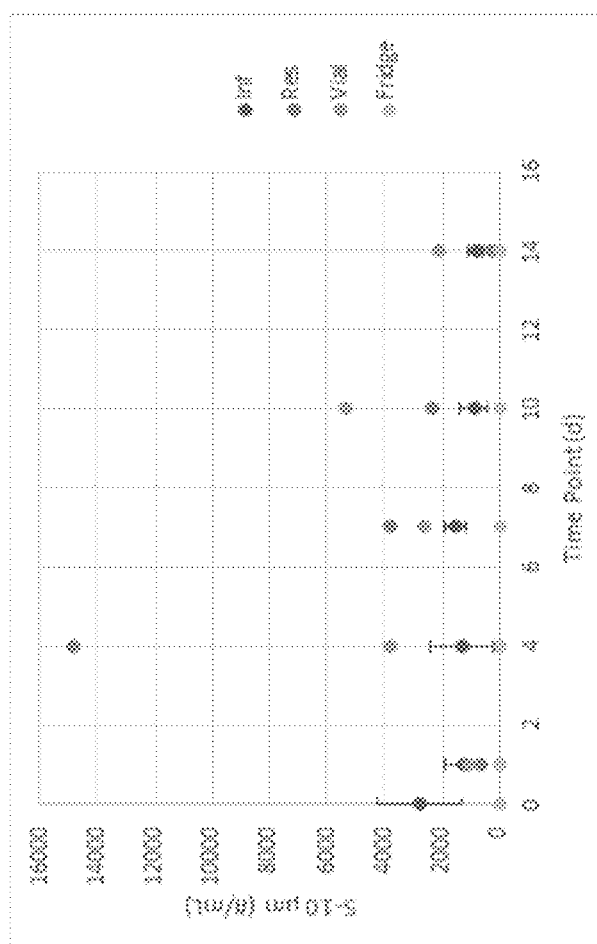
FIG. 14 shows data comparing particulate matter found in various substances.

FIG. 14 shows data showing particulate matter collected from undelivered medication 1302, medication from a reservoir of a delivery system as described herein 1304, infusate medication 1306, and a control 1308. As shown in this figure, the infusate 1306 has much lower levels of particulate aggregation than the medication from the reservoir 1304, again demonstrating the efficacy of the filtering described herein.

In other embodiments, the particulate trap can include a non-circular lumen in the insulin delivery system with high-flow-resistance zones, such as star shape with acute-angle corners, configured so that the particulates collect in the resistance zones.

In other embodiments, the particulate trap can include features in the fluid path that cause mixing (mildly turbulent flow) near the center of the flow channel will facilitate particulate capture at the edges.

In other embodiments, the particulate trap can include a dead-end flow path (e.g., with preservative barrier properties) where non-dissolved particulate material will accumulate. In other embodiments, the particulate trap can include an inner surface of the fluid path of the insulin delivery system that is configured to specifically adhere silicone oil droplets, which can, in turn, capture insulin fibrils.

In other embodiments, the particulate trap can include a serpentine flow path, such as made of cured-in-place foam or open-cell foam lumen.

In other embodiments, the particulate trap can include lengthwise fibers threaded into the lumen where capture properties are included on the fibers (surface finish, chemistry, combination). The fibers, for example, can be pulled through the lumen using pressure differential across the length of the tubing.

In some embodiments, the particulate trap can include a flow path with high surface area.

In other embodiments, the particulate trap can include a conical cavity built into the flow path with flow dynamics designed to achieve cyclonic separation of particulates from dissolved material (e.g., such that captured particulates are directed into a sink at the tip of the cone).

In other embodiments, the particulate trap can include an affinity surface (e.g., hydrophobic, adhesive, fibril antibodies, aptamers, molecular templates) generated by chemical manipulation after extrusion. In other embodiments, the particulate trap can include a filler material in an inner lumen (e.g., carbon black, carbon tubules, ceramic nanoparticles) that protrude into the fluid path and acts as a trap for large molecular species, but permit the passage of insulin hexamer and smaller molecules.

In other embodiments, the particulate trap can include a highly hydrophobic inner surface. In other embodiments, the particulate trap can be part of a dual-lumen infusion set with a filtration membrane between the lumens (e.g., a hollow fiber filter within a larger tubing).

It should be understood that any feature described herein with respect to one embodiment can be used in addition to or in place of any feature described with respect to another embodiment.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An insulin delivery system comprising:
   a reservoir configured to hold an insulin medication therein;
   an infusion hub;
   tubing connecting the insulin reservoir and the infusion hub;
   a cannula configured to deliver the insulin medication to a patient; and
   a filter configured to capture particulates from the insulin medication prior to delivery of the insulin to the patient, wherein the filter comprises an internal coil within the cannula.

2. The insulin delivery system of claim 1, wherein the internal coil comprises a round wire.

3. The insulin delivery system of any of claim 1, wherein the internal coil comprises a flat wire.

4. The insulin delivery system of any of claim 1, wherein the internal coil comprises an engineering polymer.

5. The insulin delivery system of any of claim 1, wherein the internal coil comprises stainless steel.

6. The insulin delivery system of any of claim 1, wherein the filter comprises a structural component to prevent crushing or kinking of the extruded cannula.

7. The insulin delivery system of claim 1, further comprising an absorbent element positioned within the delivery system and in fluidic contact with the insulin medication, the absorbent element configured to absorb and store preservatives from the insulin medication.

8. The insulin delivery system of claim 7, further comprising an impermeable backing layer adjacent to the absorbent element and configured to maintain the preservatives within the absorbent.

9. The insulin delivery system of any of claim 7, wherein the absorbent element comprises EVOH, silicone, a low-density polymer, a PEG block-copolymer (e.g., PETG), PET, nylon, a nylon block-copolymer, a polymeric foam, or a polymeric monolith.

10. The insulin delivery system of claim 7, wherein the absorbent comprises a preservative capacity greater than a maximum concentration of preservative in the insulin medication.

11. The insulin delivery system of claim 7, wherein the absorbent is further configured to release preservatives to the insulin medication after storing the preservatives.

12. The insulin delivery system of claim 7, wherein the absorbent is configured to maintain the preservative concentration at the point of delivery to the patient at a concentration that minimizes local toxicity while maintaining insulin in a stable hexameric state.

13. The insulin delivery system of claim 7, wherein the absorbent comprises an interior layer of the tubing.

14. The insulin delivery system of any of claim 1, wherein at least a portion of the insulin delivery system includes a barrier layer configured to prevent migration of preservatives from the insulin medication.

15. The insulin delivery system of claim 14, wherein the tubing is a multi-layer tubing, and wherein the barrier layer is at least a portion of a layer of the multi-layer tubing.

16. The insulin delivery system of claim 14, wherein the tubing is a multi-layer tubing, and wherein the barrier layer forms an entire layer of the multi-layer tubing.

17. The insulin delivery system of claim 14, wherein the barrier layer comprises a coating on the tubing.

18. The insulin delivery system of claim 14, wherein the barrier layer comprises an inner layer of the tubing.

19. The insulin delivery system of claim 14, wherein the barrier layer comprises polyether block-amide, HDPE, polypropylene, PTFE, chloro- and fluorosilicones, hydrochloro-, hydrofluoro-, and perfluoro-polymers, chlorinated polymers (e.g. viton), metal-coated polymers (e.g., mylar), poly carbonate, organic or inorganic plasma-deposited coatings (e.g. PTFE, PVC, halogenated siloxanes, silicon suboxides), vapor-deposited coatings (such as nitrides, titanium nitride, fluorocarbons, metals), Kapton, or parylene.

20. The insulin delivery system of claim 14, further comprising a barrel connected to the cannula, and wherein the barrier layer is positioned on at least a portion of the barrel.

21. The insulin delivery system of claim 14, comprising a connector comprising the barrier layer.

22. The insulin delivery system of claim 14, wherein the barrier layer extends through an entire fluid path of the system.

23. The insulin delivery system of claim 14, further comprising a vent in the tubing or the hub configured to release preservatives from the insulin medication prior to delivery of the insulin medication to the patient.

24. The insulin delivery system of claim 23, wherein at least a portion of the insulin delivery system includes a barrier layer configured to prevent migration of preservatives from the insulin medication and wherein the vent comprises an opening in the barrier layer.

25. The insulin delivery system of claim 23, wherein at least a portion of the insulin delivery system includes a barrier layer configured to prevent migration of preservatives from the insulin medication and wherein the vent comprises a portion of the barrier layer that is thinner than other portions of the barrier layer.

26. An insulin delivery system comprising:
a reservoir configured to hold an insulin medication therein;
an infusion hub;
tubing connecting the insulin reservoir and the infusion hub;
a cannula configured to deliver the insulin medication to a patient; and
a filter configured to capture particulates from the insulin medication prior to delivery of the insulin to the patient,
wherein the filter comprises features internal to the cannula and in fluidic contact with the insulin configured to affect hydrodynamic flow characteristics of insulin medication flowing within the cannula and to create pressure differential regimes to promote the capture and retention of aggregate particles that have formed out of solution.

27. The insulin delivery system of any of claim 26, wherein the features comprise internally molded features within the cannula.

28. The insulin delivery system of any of claim 26, wherein the features comprise internally extruded features within the cannula.

29. The insulin delivery system of any of claim 26, wherein the filter comprises a threaded inner surface of the cannula.

30. The insulin delivery system of claim 26, wherein the features repeat along at least a portion of a length of the cannula.

31. The insulin delivery system of claim 30, wherein a ratio of a width of the features and a period of the features is greater than about 1:1 and less than about 1:4.

32. A method for delivering insulin, comprising:
providing a delivery system;
delivering insulin medication comprising preservatives from a reservoir through tubing connecting the reservoir to an infusion hub;
filtering the insulin medication to capture particulates from the insulin medication prior to delivery of the insulin medication to the patient; and
delivering the insulin medication to the patient through a cannula connected to the infusion hub,
wherein filtering the insulin medication comprises using a coil internal to the cannula, the coil configured to create a region of features affecting hydrodynamic flow characteristics of insulin medication flowing within the cannula and creating differential pressure regimes to promote the capture and retention of aggregate particles that have formed out of solution.

33. The method of claim 32, wherein the coil comprises a round wire.

34. The method of claim 32, wherein the coil comprises a flat wire.

35. The method of claim 32, further comprising exposing the insulin medication to an absorbent element configured to store preservatives from the insulin medication.

36. The method of claim 35, further comprising the absorbent element absorbing preservatives from the insulin medication.

37. The method of claim 35, further comprising the absorbent element releasing preservatives back into the insulin medication.

38. The method of claim 35, further comprising preventing preservative evaporation using a barrier layer on one or more components of the delivery system.

39. The method of claim 32, further comprising venting the insulin medication, thereby releasing preservatives from the insulin medication.

40. The method of claim 39, further comprising preventing preservative loss from the insulin medication by providing a barrier layer along at least a portion of the fluid path of the delivery system, and wherein venting the insulin medication comprises exposing the insulin medication to an opening in the barrier layer.

41. The method of claim 39, further comprising preventing preservative loss from the insulin medication by providing a barrier layer along at least a portion of the fluid path of the delivery system, and wherein venting the insulin medication comprises exposing the insulin medication to a portion of the barrier layer that is thinner than other portions of the barrier layer.

42. A method for delivering insulin, comprising:
providing a delivery system;
delivering insulin medication comprising preservatives from a reservoir through tubing connecting the reservoir to an infusion hub;
filtering the insulin medication to capture particulates from the insulin medication prior to delivery of the insulin medication to the patient; and
delivering the insulin medication to the patient through a cannula connected to the infusion hub,
wherein filtering the insulin medication comprises providing, within a flow path of the insulin medication, features internal to the cannula, thereby affecting hydrodynamic flow characteristics of insulin medication flowing within the cannula and creating differential pressure regimes to promote the capture and retention of aggregate particles that have formed out of solution.

\* \* \* \* \*